(12) United States Patent
Belancio et al.

(10) Patent No.: US 10,371,703 B2
(45) Date of Patent: Aug. 6, 2019

(54) ANTIBODIES THAT INHIBIT LONG INTERSPERSED ELEMENT-1 RETROTRANSPOSON ENDONUCLEASE ACTIVITY

(71) Applicants: Victoria Perepelitsa Belancio, New Orleans, LA (US); Mark Sokolowski, New Orleans, LA (US)

(72) Inventors: Victoria Perepelitsa Belancio, New Orleans, LA (US); Mark Sokolowski, New Orleans, LA (US)

(*) Notice: Subject to any disclaimer, the term of this patent is extended or adjusted under 35 U.S.C. 154(b) by 265 days.

(21) Appl. No.: 14/943,942

(22) Filed: Nov. 17, 2015

(65) Prior Publication Data

US 2016/0258955 A1     Sep. 8, 2016

Related U.S. Application Data

(60) Provisional application No. 62/081,259, filed on Nov. 18, 2014.

(51) Int. Cl.
| | |
|---|---|
| *G01N 33/53* | (2006.01) |
| *G01N 33/573* | (2006.01) |
| *C07K 16/40* | (2006.01) |
| *G01N 33/68* | (2006.01) |

(52) U.S. Cl.
CPC ........... *G01N 33/573* (2013.01); *C07K 16/40* (2013.01); *G01N 33/6863* (2013.01); *C07K 2317/33* (2013.01); *C07K 2317/76* (2013.01); *C12Y 301/21* (2013.01); *G01N 2333/922* (2013.01)

(58) Field of Classification Search
CPC ............. G01N 33/573; G01N 33/6863; G01N 2333/922; C07K 16/40; C07K 2317/76; C07K 2317/33; C12Y 301/21
See application file for complete search history.

(56) References Cited

U.S. PATENT DOCUMENTS

2003/0003468 A1* 1/2003 Crow ................. C12N 15/1034
                                                                435/6.14

OTHER PUBLICATIONS

Sokoloski et al., (Mobile DNA 2014, 5:29 published on line Dec. 10, 2014).*
Pandey (International Journal of Pharmaceutical Sciences Review and Research, vol. 1, Issue 2, Mar.-Apr. 2010; Article 017.*
Weichenrieder, Structure, vol. 12, 975-986, Jun. 2004,.*
Current Protocols in Cell Biology, Current Protocols in Cell Biology (2000) 16.5.1-16.5.22 edited by by John Wiley & Sons, Inc. retrieved from http://web4.cbm.uam.es/joomla-rl/images/Servicios/070.Microscopia-optica-cfocal/documentos/conjugacion_anticuerpos.pdf.*
Brown et al , J. Immuno. May 1996, 3285-91.*
Vajdos et al. , J. Mol. Biol. Jul. 5, 2002, 320(2):415-28.*
Douchet, A., et al., Characterization of Line-1 Ribonucleoprotein Particles, PLoS Genetics, 2010, p. e1001150, vol. 6, issue 10.
Ergun, S., et al., Cell Type-specific Expression of LINE-1 Open Reading Frames 1 and 2 in Fetal and Adult Human Tissues, Journal of Biological Chemistry, 2004, p. 27753, vol. 279, issue 26.
Goodier, J., et al., A potential role for the nucleolus in L1 retrotransposition, Human Molecular Genetics, 2004, p. 1041, vol. 13, issue 10.
Kines, K., et al., Potential for genomic instability associated with retrotranspositionally-incompetent L1 loci, Nucleic Acids Research, epub Aug. 2014, p. 10488, vol. 42, issue 16.
Wagstaff, B., et al., Molecular Reconstruction of Extinct LINE-1 Elements and Their Interaction with Nonautonomous Elements, Mol. Biol. Evol., 2012, p. 88, vol. 30, issue 1.

* cited by examiner

*Primary Examiner* — Julie Wu
*Assistant Examiner* — Carmencita M Belei
(74) *Attorney, Agent, or Firm* — Laurence J. Hyman; Hyman IP Law

(57) ABSTRACT

The present disclosure relates to monoclonal anti-LINE-1 ORF2 protein endonuclease domain antibody, and fragments and derivatives that bind the LINE-1 ORF2 protein endonuclease domain and inhibit its activity.

18 Claims, 12 Drawing Sheets

Specification includes a Sequence Listing.

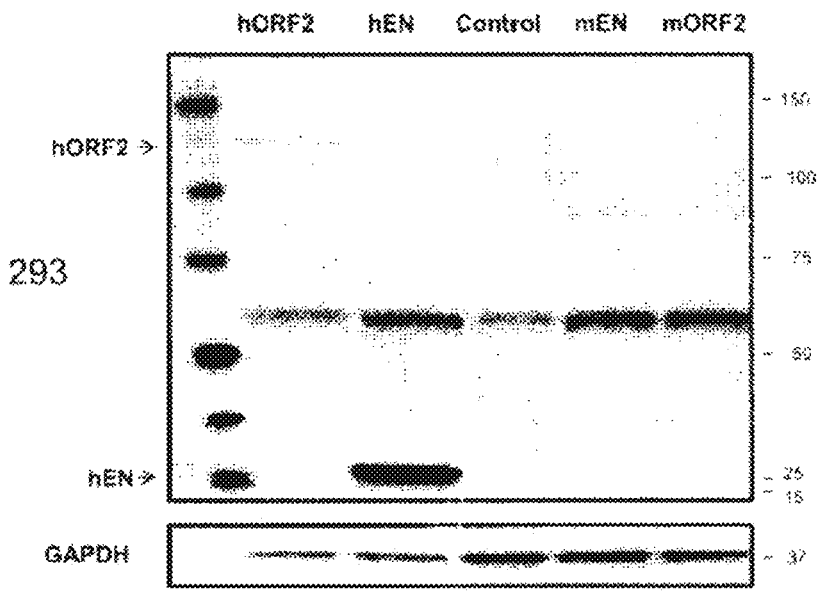
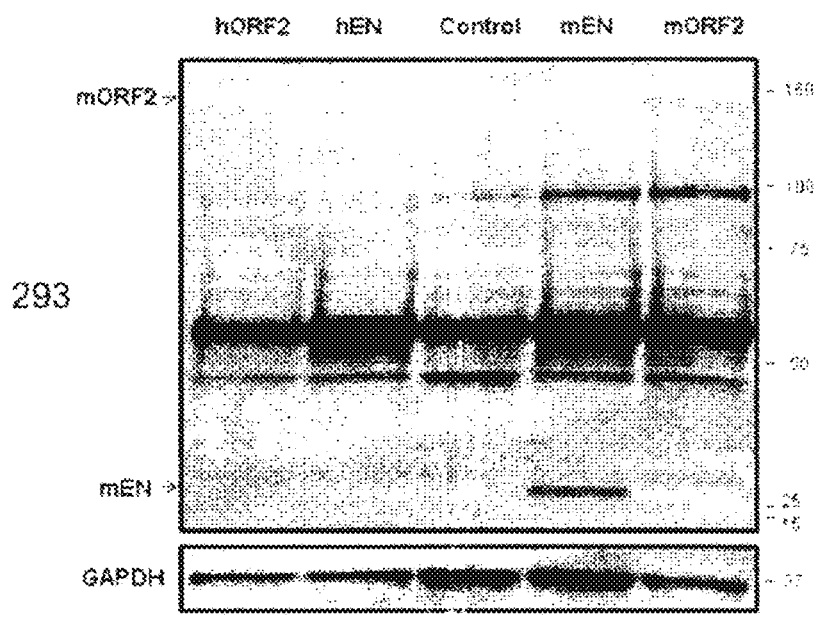

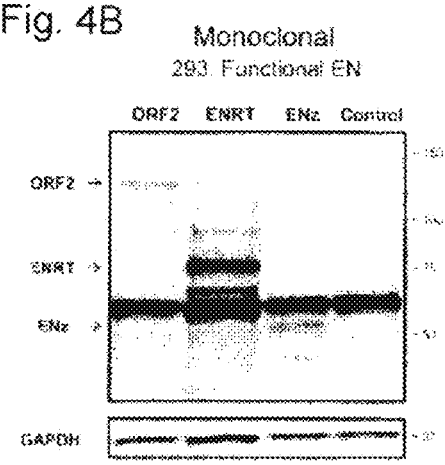
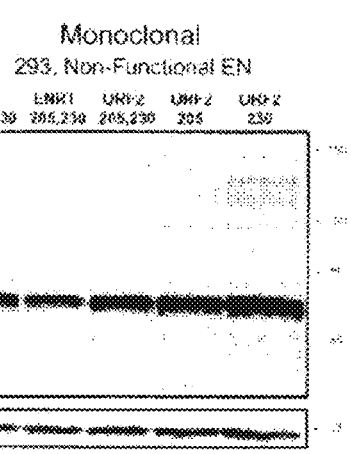
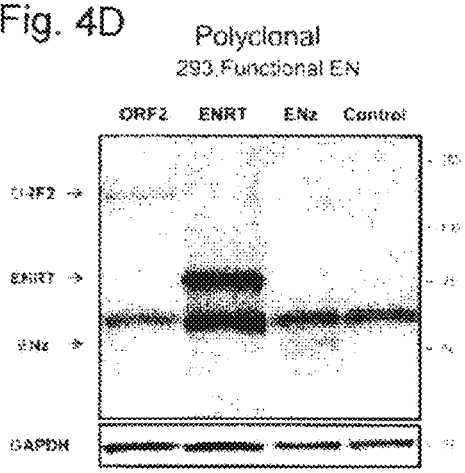
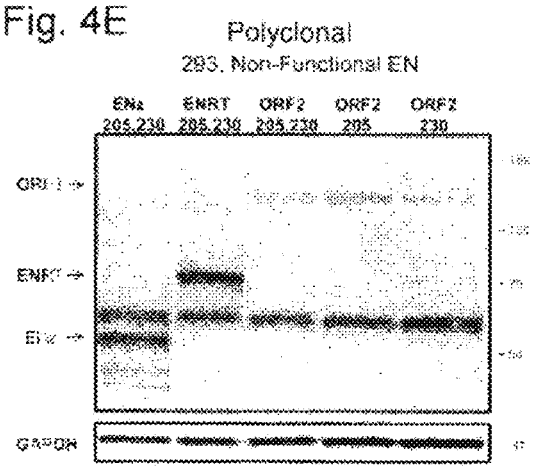

Fig. 7B
Fig. 7C
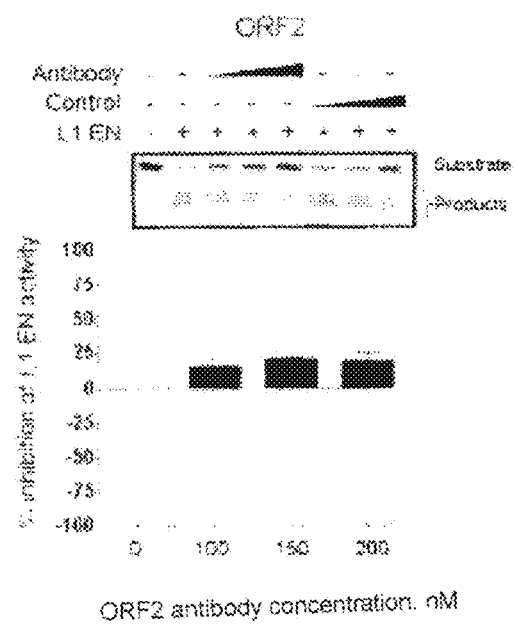
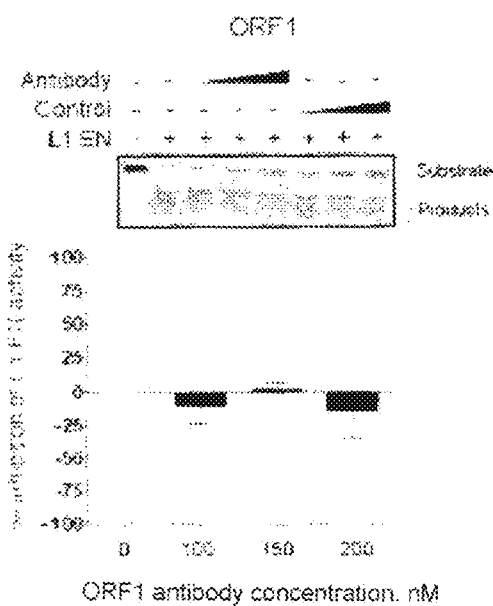

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Glu Trp Ile Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctttttttt taaccgc                                                  17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcggttaaaa aaaaagg                                                  17

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Abasic nucleotide

<400> SEQUENCE: 5
gcccccnggg gacgtacgat atcccgctcc                                    30

<210> SEQ ID NO 6
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 6
ggagcgggat atcgtacgtc ccccgggggc                                    30

<210> SEQ ID NO 7
<211> LENGTH: 239
<212> TYPE: PRT
<213> ORGANISM: Homo sapiens

<400> SEQUENCE: 7

Met Thr Gly Ser Asn Ser His Ile Thr Ile Leu Thr Leu Asn Ile Asn
1               5                   10                  15

Gly Leu Asn Ser Ala Ile Lys Arg His Arg Leu Ala Ser Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Ala Gly Val Ala Ile Leu Val Ser Asp
65                  70                  75                  80

Lys Thr Asp Phe Lys Pro Thr Lys Ile Lys Arg Asp Lys Glu Gly His
                85                  90                  95

Tyr Ile Met Val Lys Gly Ser Ile Gln Gln Glu Leu Thr Ile Leu
            100                 105                 110

Asn Ile Tyr Ala Pro Asn Thr Gly Ala Pro Arg Phe Ile Lys Gln Val
        115                 120                 125

Leu Ser Asp Leu Gln Arg Asp Leu Asp Ser His Thr Leu Ile Met Gly
    130                 135                 140

Asp Phe Asn Thr Pro Leu Ser Thr Leu Asp Arg Ser Thr Arg Gln Lys
145                 150                 155                 160

Val Asn Lys Asp Thr Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
        195                 200                 205

Gly Ser Lys Ala Leu Leu Ser Lys Cys Lys Arg Thr Glu Ile Ile Thr
    210                 215                 220

Asn Tyr Leu Ser Asp His Ser Ala Ile Lys Leu Glu Leu Arg Ile
225                 230                 235

<210> SEQ ID NO 8
<211> LENGTH: 239
<212> TYPE: PRT
<213> ORGANISM: Homo sapiens

<400> SEQUENCE: 8

Met Thr Gly Ser Asn Ser His Ile Thr Ile Leu Thr Leu Asn Val Asn
1               5                   10                  15

Gly Leu Asn Ala Pro Ile Lys Arg His Arg Leu Ala Asn Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

```
Ala Asn Gly Lys Gln Lys Lys Ala Gly Val Ala Ile Leu Val Ser Asp
 65                  70                  75                  80

Lys Thr Asp Phe Lys Pro Thr Lys Ile Lys Arg Asp Lys Glu Gly His
                 85                  90                  95

Tyr Ile Met Val Lys Gly Ser Ile Gln Gln Glu Glu Leu Thr Ile Leu
            100                 105                 110

Asn Ile Tyr Ala Pro Asn Thr Gly Ala Pro Arg Phe Ile Lys Gln Val
            115                 120                 125

Leu Ser Asp Leu Gln Arg Asp Leu Asp Ser His Thr Leu Ile Met Gly
        130                 135                 140

Asp Phe Asn Thr Pro Leu Ser Thr Leu Asp Arg Ser Thr Arg Gln Lys
145                 150                 155                 160

Val Asn Lys Asp Thr Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Leu
            195                 200                 205

Gly Ser Lys Ala Leu Leu Ser Lys Cys Lys Arg Thr Glu Ile Ile Thr
210                 215                 220

Asn Tyr Leu Ser Asp His Ser Ala Ile Lys Leu Glu Leu Arg Ile
225                 230                 235

<210> SEQ ID NO 9
<211> LENGTH: 239
<212> TYPE: PRT
<213> ORGANISM: Homo sapiens

<400> SEQUENCE: 9

Met Thr Gly Ser Asn Ser His Ile Thr Ile Leu Thr Leu Asn Val Asn
  1               5                  10                  15

Gly Leu Asn Ala Pro Ile Lys Arg His Arg Leu Ala Asn Trp Ile Lys
             20                  25                  30

Ser Gln Asp Pro Ser Val Cys Cys Ile Gln Glu Thr His Leu Thr Cys
         35                  40                  45

Arg Asp Thr His Arg Leu Lys Ile Lys Gly Trp Arg Lys Ile Tyr Gln
 50                  55                  60

Ala Asn Gly Lys Gln Lys Lys Ala Gly Val Ala Ile Leu Val Ser Asp
 65                  70                  75                  80

Lys Thr Asp Phe Lys Pro Thr Lys Ile Lys Arg Asp Lys Glu Gly His
                 85                  90                  95

Tyr Ile Met Val Lys Gly Ser Ile Gln Gln Glu Glu Leu Thr Ile Leu
            100                 105                 110

Asn Ile Tyr Ala Pro Asn Thr Gly Ala Pro Arg Phe Ile Lys Gln Val
            115                 120                 125

Leu Ser Asp Leu Gln Arg Asp Leu Asp Ser His Thr Ile Ile Met Gly
        130                 135                 140

Asp Phe Asn Thr Pro Leu Ser Thr Leu Asp Arg Ser Thr Arg Gln Lys
145                 150                 155                 160

Val Asn Lys Asp Thr Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
```

```
              195                 200                 205
Gly Ser Lys Ala Leu Leu Ser Lys Cys Lys Arg Thr Glu Ile Ile Thr
            210                 215                 220

Asn Cys Leu Ser Asp His Ser Ala Ile Lys Leu Glu Leu Arg Ile
225                 230                 235
```

<210> SEQ ID NO 10
<211> LENGTH: 239
<212> TYPE: PRT
<213> ORGANISM: Homo sapiens

<400> SEQUENCE: 10

```
Met Thr Gly Ser Asn Ser His Ile Thr Ile Leu Thr Leu Asn Val Asn
1               5                   10                  15

Gly Leu Asn Ala Pro Ile Lys Arg His Arg Leu Ala Asn Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Lys Ala Gly Val Ala Ile Leu Val Ser Asp
65                  70                  75                  80

Lys Thr Asp Phe Lys Pro Thr Lys Ile Lys Arg Asp Lys Glu Gly His
                85                  90                  95

Tyr Ile Met Val Lys Gly Ser Ile Gln Gln Glu Leu Thr Ile Leu
            100                 105                 110

Asn Ile Tyr Ala Pro Asn Thr Gly Ala Pro Arg Phe Ile Lys Gln Val
        115                 120                 125

Leu Ser Asp Leu Gln Arg Asp Leu Asp Ser His Thr Ile Met Gly
130                 135                 140

Asp Phe Asn Thr Pro Leu Ser Thr Leu Asp Arg Ser Thr Arg Gln Lys
145                 150                 155                 160

Val Asn Lys Asp Ile Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
        195                 200                 205

Gly Ser Lys Ala Leu Leu Ser Lys Cys Lys Arg Thr Glu Ile Ile Thr
            210                 215                 220

Asn Cys Leu Ser Asp His Ser Ala Ile Lys Leu Glu Leu Arg Ile
225                 230                 235
```

<210> SEQ ID NO 11
<211> LENGTH: 239
<212> TYPE: PRT
<213> ORGANISM: Homo sapiens

<400> SEQUENCE: 11

```
Met Thr Gly Ser Asn Ser His Ile Thr Ile Leu Thr Leu Asn Val Asn
1               5                   10                  15

Gly Leu Asn Ala Pro Ile Lys Arg His Arg Leu Ala Asn Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
```

```
                    50                  55                  60
Ala Asn Gly Lys Gln Lys Lys Ala Gly Val Ala Ile Leu Val Ser Asp
 65                  70                  75                  80

Lys Thr Asp Phe Lys Pro Thr Lys Ile Lys Arg Asp Lys Glu Gly His
                 85                  90                  95

Tyr Ile Met Val Lys Gly Ser Ile Gln Gln Glu Glu Leu Thr Ile Leu
                100                 105                 110

Asn Ile Tyr Ala Pro Asn Thr Gly Ala Pro Arg Phe Ile Lys Gln Val
            115                 120                 125

Leu Arg Asp Leu Gln Arg Asp Leu Asp Ser His Thr Ile Ile Met Gly
130                 135                 140

Asp Phe Asn Thr Pro Leu Ser Thr Leu Asp Arg Ser Thr Arg Gln Lys
145                 150                 155                 160

Val Asn Lys Asp Ile Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
        195                 200                 205

Gly Ser Lys Ala Leu Leu Ser Lys Cys Lys Arg Thr Glu Ile Ile Thr
210                 215                 220

Asn Cys Leu Ser Asp His Ser Ala Ile Lys Leu Glu Leu Arg Ile
225                 230                 235

<210> SEQ ID NO 12
<211> LENGTH: 239
<212> TYPE: PRT
<213> ORGANISM: Homo sapiens

<400> SEQUENCE: 12

Met Thr Gly Ser Asn Ser His Ile Thr Ile Leu Thr Leu Asn Val Asn
 1                   5                  10                  15

Gly Leu Asn Ala Pro Ile Lys Arg His Arg Leu Ala Asn Trp Ile Lys
                 20                  25                  30

Ser Gln Asp Pro Ser Val Cys Cys Ile Gln Glu Thr His Leu Thr Cys
             35                  40                  45

Arg Asp Thr His Arg Leu Lys Ile Lys Gly Trp Arg Lys Ile Tyr Gln
 50                  55                  60

Ala Asn Gly Lys Gln Lys Lys Ala Gly Val Ala Ile Leu Val Ser Asp
 65                  70                  75                  80

Lys Thr Asp Phe Lys Pro Thr Lys Ile Lys Arg Asp Lys Glu Gly His
                 85                  90                  95

Tyr Ile Met Val Lys Gly Ser Ile Gln Gln Glu Glu Leu Thr Ile Leu
                100                 105                 110

Asn Ile Tyr Ala Pro Asn Thr Gly Ala Pro Arg Phe Ile Lys Gln Val
            115                 120                 125

Leu Arg Asp Leu Gln Arg Asp Leu Asp Ser His Thr Ile Ile Met Gly
130                 135                 140

Asp Phe Asn Thr Pro Leu Ser Ile Leu Asp Arg Ser Thr Arg Gln Lys
145                 150                 155                 160

Val Asn Lys Asp Ile Gln Asp Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190
```

```
Phe Phe Ser Ala Pro His Arg Thr Tyr Ser Lys Ile Asp His Ile Ile
            195                 200                 205

Gly Ser Lys Ala Leu Leu Ser Lys Cys Lys Arg Thr Glu Ile Thr Thr
210                 215                 220

Asn Cys Leu Ser Asp His Ser Ala Ile Lys Leu Glu Leu Arg Ile
225                 230                 235

<210> SEQ ID NO 13
<211> LENGTH: 239
<212> TYPE: PRT
<213> ORGANISM: Homo sapiens

<400> SEQUENCE: 13

Met Thr Gly Ser Asn Ser His Ile Thr Ile Leu Thr Leu Asn Val Asn
1               5                   10                  15

Gly Leu Asn Ala Pro Ile Lys Arg His Arg Leu Ala Asn Trp Ile Lys
            20                  25                  30

Ser Gln Asp Pro Ser Val Cys Cys Ile Gln Glu Thr His Leu Thr Cys
        35                  40                  45

Lys Asp Thr His Arg Leu Lys Ile Lys Gly Trp Arg Lys Ile Tyr Gln
50                  55                  60

Ala Asn Gly Lys Gln Lys Lys Ala Gly Val Ala Ile Leu Val Ser Asp
65                  70                  75                  80

Lys Thr Asp Phe Lys Pro Thr Lys Ile Lys Lys Asp Lys Glu Gly His
                85                  90                  95

Tyr Ile Met Val Lys Gly Ser Met Gln Gln Glu Glu Leu Thr Ile Leu
            100                 105                 110

Asn Ile Tyr Ala Pro Asn Thr Gly Ala Pro Arg Phe Ile Lys Gln Val
        115                 120                 125

Leu Arg Asp Leu Gln Arg Asp Leu Asp Ser His Thr Ile Ile Val Gly
    130                 135                 140

Asp Phe Asn Thr Pro Leu Ser Ile Leu Asp Arg Ser Thr Arg Gln Lys
145                 150                 155                 160

Ile Asn Lys Asp Ile Gln Asp Leu Asn Ser Ala Leu Asp Gln Ala Asp
                165                 170                 175

Leu Ile Asp Val Tyr Arg Thr Leu His Pro Lys Ser Thr Glu Tyr Thr
            180                 185                 190

Phe Phe Ser Ala Pro His Arg Thr Tyr Ser Lys Ile Asp His Ile Ile
        195                 200                 205

Gly Ser Lys Thr Leu Leu Ser Lys Cys Lys Arg Thr Glu Ile Ile Thr
    210                 215                 220

Asn Ser Leu Ser Asp His Ser Ala Ile Lys Leu Glu Leu Arg Ile
225                 230                 235

<210> SEQ ID NO 14
<211> LENGTH: 239
<212> TYPE: PRT
<213> ORGANISM: Homo sapiens

<400> SEQUENCE: 14

Met Thr Gly Ser Asn Ser His Ile Thr Ile Leu Thr Leu Asn Val Asn
1               5                   10                  15

Gly Leu Asn Ala Pro Ile Lys Arg His Arg Leu Ala Asn Trp Ile Lys
            20                  25                  30

Ser Gln Asp Pro Ser Val Cys Cys Ile Gln Glu Thr His Leu Met Cys
        35                  40                  45
```

```
Lys Asp Thr His Arg Leu Lys Ile Lys Gly Trp Arg Asn Ile Tyr Gln
 50                  55                  60

Ala Asn Gly Lys Gln Lys Lys Ala Gly Val Ala Ile Leu Val Ser Asp
 65                  70                  75                  80

Lys Thr Asp Phe Lys Pro Thr Lys Ile Lys Asp Lys Glu Gly His
                 85                  90                  95

Tyr Ile Met Val Asn Gly Ser Thr Gln Gln Glu Glu Leu Thr Ile Leu
             100                 105                 110

Asn Ile Tyr Ala Pro Asn Thr Gly Ala Pro Arg Phe Ile Lys Gln Val
             115                 120                 125

Leu Arg Asp Leu Gln Arg Asp Leu Asp Ser His Thr Ile Ile Val Gly
130                 135                 140

Asp Phe Asn Thr Pro Leu Ser Ile Leu Asp Arg Ser Thr Arg Gln Lys
145                 150                 155                 160

Ile Asn Lys Asp Ile Gln Asp Leu Asn Ser Ala Leu Asp Gln Val Asp
                165                 170                 175

Leu Ile Asp Ile Tyr Arg Thr Leu His Pro Lys Ser Thr Glu Tyr Thr
            180                 185                 190

Phe Phe Ser Ala Pro His Ser Thr Tyr Ser Lys Ile Asp His Ile Ile
        195                 200                 205

Gly Ser Lys Thr Leu Leu Ser Lys Cys Lys Arg Thr Glu Ile Ile Thr
210                 215                 220

Asn Ser Leu Ser Asp His Ser Ala Ile Lys Leu Glu Leu Arg Ile
225                 230                 235

<210> SEQ ID NO 15
<211> LENGTH: 258
<212> TYPE: PRT
<213> ORGANISM: Mus sp.

<400> SEQUENCE: 15

Met Pro Pro Leu Thr Thr Lys Ile Thr Gly Ser Asn Asn Tyr Phe Ser
 1               5                  10                  15

Leu Ile Ser Leu Asn Ile Asn Gly Leu Asn Ser Pro Ile Lys Arg His
             20                  25                  30

Arg Leu Thr Asn Trp Leu His Lys Gln Asp Pro Thr Phe Cys Cys Leu
         35                  40                  45

Gln Glu Thr His Leu Arg Glu Lys Asp Arg His Tyr Leu Arg Met Lys
 50                  55                  60

Gly Trp Lys Thr Ile Phe Gln Ala Asn Gly Met Lys Lys Gln Ala Gly
 65                  70                  75                  80

Val Ala Ile Leu Ile Ser Asp Lys Ile Asp Phe Gln Pro Lys Val Ile
             85                  90                  95

Lys Lys Asp Lys Glu Gly His Phe Ile Leu Ile Lys Gly Lys Ile Leu
            100                 105                 110

Gln Glu Glu Leu Ser Ile Leu Asn Ile Tyr Ala Pro Asn Thr Arg Ala
            115                 120                 125

Ala Thr Phe Thr Lys Glu Thr Leu Val Lys Leu Lys Ala His Ile Ala
130                 135                 140

Pro His Thr Ile Ile Val Gly Asp Phe Asn Thr Pro Leu Ser Pro Met
145                 150                 155                 160

Asp Arg Ser Trp Lys Gln Lys Leu Asn Arg Asp Thr Leu Lys Leu Thr
                165                 170                 175

Glu Val Met Lys Gln Met Asp Leu Thr Asp Ile Tyr Arg Thr Phe Tyr
            180                 185                 190
```

-continued

```
Pro Lys Thr Lys Gly Tyr Thr Phe Phe Ser Ala Pro His Gly Thr Phe
    195                 200                 205
Ser Lys Ile Asp His Ile Ile Gly His Lys Ser Gly Leu Asn Arg Leu
    210                 215                 220
Lys Asn Ile Glu Ile Val Pro Cys Ile Leu Ser Asp His His Ala Leu
225             230                 235                 240
Arg Leu Ile Phe Asn Asn Lys Ile Asn Asn Arg Lys Pro Thr Phe Thr
                245                 250                 255
Trp Lys
```

US 10,371,703 B2

ANTIBODIES THAT INHIBIT LONG INTERSPERSED ELEMENT-1 RETROTRANSPOSON ENDONUCLEASE ACTIVITY

CROSS-REFERENCE TO RELATED APPLICATIONS

This application claims the benefit and priority of U.S. Provisional Patent Application No. 62/081,259, filed Nov. 18, 2014, the contents of which are hereby incorporated by reference in their entirety.

STATEMENT OF FEDERAL FUNDING

The invention was made with U.S. Government support under Grant P20GM10342, awarded by the National Institute of General Medical Sciences. The government has certain rights in the invention.

PARTIES TO JOINT RESEARCH AGREEMENT

Not applicable.

REFERENCE TO SEQUENCE LISTING OR TABLE SUBMITTED ON COMPACT DISC AND INCORPORATION-BY-REFERENCE OF THE MATERIAL

The instant application contains a Sequence Listing which has been submitted electronically in ASCII format and is hereby incorporated by reference in its entirety. The ASCII copy, created on Apr. 18, 2016, is named TU-000510US_SL.txt and is 20,786 bytes in size.

BACKGROUND OF THE INVENTION

Long interspersed element-1 (L1) is an autonomous non-long terminal repeat retrotransposon that has parasitized the human genome for millions of years. L1 has shaped the evolution of the human genome through a copy-and-paste mobilization of itself (Moran et al., Cell 1996, 87(5):917-927) as well as the short interspersed element (SINE) Alu, SINE-VNTR-Alu elements (SVA), and processed cellular transcripts (Dewannieux et al., Nat Genet 2003, 35(1):41-48; Ostertag et al., Amer J Human Genetics 2003, 73(6):1444-1451, Esnault et al., Nat Genet 2000, 24(4):363-367). Functional full-length L1 transcripts contain two open reading frames (ORFs) encoding ORF1 and ORF2 proteins (ORF1p and ORF2p, respectively), as seen in FIG. 1A. These L1 proteins exhibit cis-preference for their encoding L1 mRNA (Kulpa and Moran, Human Mol Genetics 2005, 14(21):3237-3248; Wei et al., Mol Cell Biol 2001, 21(4):1429-1439, Kolosha and Martin, Proc Natl Acad Sci (USA) 1997, 94(19):10155-10160), and are utilized in trans by the Alu and SVA elements (Dewannieux, supra, Ostertag, supra, Wallace et al., Gene 2008, 419(1-2):1-6). L1, Alu, and SVA form ribonucleoprotein (RNP) particles that reach the nucleus to complete their replication cycles by integrating in the host genome via a process of target-primed reverse transcription (Luan et al., Cell 1993, 72(4):595-605, Cost et al., EMBO J, 2002, 21(21):5899-5910). This copy-and-paste process has produced approximately 500,000 L1 loci, accounting for about 17% of the human genome, and over 1,000,000 copies of Alu, which comprise about 11% of the human genome (Lander et al., Nature 2001, 409(6822):860-921). The majority of the L1 loci are 5' truncated with about 80-100 full-length L1 copies demonstrated to be retrotranspositionally active (Konkel et al., Gene 2007, 390(1-2):28-38; Beck et al., Cell 2010, 141(7):1159-1170; Huang et al., Cell 2010, 141(7):1171-1182; Ewing and, Kazazian, Genome Res, 2011, 21(6):985-990; Brouha et al., Proc Natl Acad Sci (USA), 2003, 100(9):5280-5285).

L1 proteins are produced from the full-length L1 mRNA with significantly different efficiencies, mostly owing to the unconventional translation from the bicistronic L1 mRNA, shown in FIG. 1A (Basame et al., J Mol Biol, 2006, 357(2):351-357; Khazina et al., Nat Struct Mol Biol 2011, 18(9):1006-1014; Callahan et al., Nucl Acids Res, 2012, 40(2):813-827; Taylor et al., Cell 2013, 155(5):1034-1048). Detection of both L1-encoded proteins is important for understanding L1 biology because each plays a critical but different role in the L1 replication cycle. The human ORF2 protein ("ORF2p") is a 149 kilodalton (kDa) protein with three annotated domains: an N-terminal endonuclease (EN) domain, a reverse transcriptase (RT) domain, and a C-terminal domain with putative RNA binding activity (Feng et al., Cell 1996, 87(5):905-916; Xiong and Eickbush, EMBO J, 1990, 9(10):3353; Fanning et al., Biochimica et Biophysica Acta, 1987, 910(3):203-212; Piskareva et al., FEBS Open Bio 2013, 3:433-437). Human and mouse L1 ORF2 proteins exhibit a high degree of sequence homology and conservation of function, making findings in mouse model systems biologically relevant to the replication cycle of the human L1 (Alisch et al., Genes & Dev, 2006, 20(2):210-224; Li et al., Nucl Acids Res, 2006, 34(3):853-864). Much has been learned about ORF2p function in vitro and in mammalian cells using overexpressed tagged ORF2 proteins and polyclonal anti-ORF2p antibodies (Ergun et al., J Biol Chem, 2004, 279(26):27753-27763; Kines et al., Nucl Acids Res, 2014, 42(16):10488-502; Goodier et al., Human Mol Genetics, 2004, 13(10):1041-1048; Doucet et al., PLoS Genet, 2010, 6(10):e1001150).

Monoclonal antibodies that can specifically recognize human ORF2 protein would be useful to study ORF2p expression and activity. They would also be useful in understanding ORF2p impact on host genome instability and the consequences of ORF2p activity on human health. Unfortunately, despite efforts to develop monoclonal antibodies that recognize ORF2 protein, no such antibody is commercially available, nor has any group reported success in producing one.

BRIEF SUMMARY OF THE INVENTION

In a first group of embodiments, the invention provides binding reagents that specifically bind to the endonuclease domain of human long interspersed element-1 (L1) open reading frame 2 (ORF2) protein, which domain does not have an inactivating mutation at position 205. In some embodiments, the binding reagent is selected from the group consisting of (a) an antibody having complementarity determining regions (CDRs), which CDRs are the same as the CDRs of monoclonal anti-L1 ORF2 protein EN antibody, (b) a fragment of the antibody which retains L1 ORF2 protein EN binding activity, and (c) a derivative of the antibody which retains L1 ORF2 protein EN binding activity. In some embodiments, the derivative of the binding reagent is a chimeric or a humanized antibody. In some embodiments, the fragment is selected from the group consisting of a Fab, a Fab', a F(ab')$_2$, a Fv; a helix-stabilized antibody, a diabody, a single-chain Fv ("scFv"), a disulfide stabilized antibody ("dsFv"), a domain antibody ("dAb,") and a minibody. In some embodiments, the antibody is monoclonal anti-L1

ORF2 protein EN antibody (hORF2 239) or a fragment the antibody which retains L1 ORF2 protein EN binding activity. In some embodiments, the antibody is monoclonal anti-L1 ORF2 protein EN antibody (hORF2 239). In some embodiments, the fragment is selected from the group consisting of a Fab, a Fab', a F(ab')$_2$, a Fv; a helix-stabilized antibody, a diabody, a single-chain Fv ("scFv"), a disulfide stabilized antibody ("dsFv"), a domain antibody ("dAb,") and a minibody. In some embodiments, the binding reagent is labeled with a detectable label. In some embodiments, the label is conjugated to said binding reagent. In some embodiments, the label is fused to the binding reagent.

In a further group of embodiments, the invention provides hybridomas producing a monoclonal antibody which specifically binds to human long interspersed element-1 (L1) open reading frame 2 (ORF2) protein having an endonuclease (EN) domain without an inactivating mutation at position 205. In some embodiments, the hybridoma is HORF2 hybridoma.

In yet a further group of embodiments, the invention provides methods of detecting whether human long interspersed element-1 (L1) open reading frame 2 (ORF2) protein having an endonuclease (EN) domain without an inactivating mutation at position 205 is present in a sample. In some embodiments, the method comprises contacting the sample with a binding regent which specifically binds to human L1ORF2 protein with said EN domain, which binding reagent is selected from the group consisting of (a) an antibody having complementarity determining regions (CDRs), which CDRs are the same as the CDRs of monoclonal anti-L1 ORF2 protein EN domain antibody, (b) a fragment of the antibody which retains L1 ORF2 protein EN domain binding activity, and (c) a derivative of said antibody which retains L1 ORF2 protein EN domain binding activity, under conditions which permit binding of the binding reagent to the protein in the sample, and detecting whether any binding reagent has bound to the protein in the sample. In some embodiments, the detection is by enzyme-linked immunosorbent assay ("ELISA"). In some embodiments, the detection is by immunoblot. In some embodiments, the antibody is a monoclonal antibody. In some embodiments, the antibody is monoclonal anti-L1 ORF2 protein EN domain antibody (hORF2 239) or a fragment said antibody which retains L1 ORF2 protein EN domain binding activity. In some embodiments, the fragment is selected from the group consisting of a Fab, a Fab', a F(ab')$_2$, a Fv; a helix-stabilized antibody, a diabody, a single-chain Fv ("scFv"), a disulfide stabilized antibody ("dsFv"), a domain antibody ("dAb,") and a minibody. In some embodiments, the binding reagent is labeled with a detectable label. In some embodiments, the label is conjugated to said binding reagent.

In still a further group of embodiments, the invention provides methods of reducing activity of human long interspersed element-1 (L1) open reading frame 2 (ORF2) protein having an endonuclease (EN) domain without an inactivating mutation at position 205 in a subject in need thereof. In some embodiments, the method comprises administering to the subject a binding regent which specifically binds to human L1ORF2 protein with the EN domain, which binding reagent is selected from the group consisting of (a) an antibody having complementarity determining regions (CDRs), which CDRs are the same as the CDRs of monoclonal anti-L1 ORF2 protein EN antibody, (b) a fragment of the antibody which retains L1 ORF2 protein EN domain binding activity, and (c) a derivative of the antibody which retains L1 ORF2 protein EN domain binding activity.

BRIEF DESCRIPTION OF THE DRAWINGS

FIG. 1A. FIG. 1A shows a schematic diagram of a full-length L1, which contains a 5' untranslated region (UTR) followed by an ORF1 sequence, an intergenic region ("IR"), an ORF2 sequence and a 3' UTR. The EN region of the ORF2 sequence subcloned to generate the purified ORF2p endonuclease (EN, 1-239aa) is indicated with a dashed box. FIG. 1B, Left panel, is a photograph of a Coomassie stained SDS-PAGE gel. Ladder (L), clarified lysate from bacteria expressing ORF2p endonuclease (CL), and final purified elution (PE) are shown. 500 ng of protein were loaded in each lane. The middle panel shows the Western blot analysis of 500 ng of CL and PE with HIS-tag specific antibodies. The ORF2p endonuclease used here has a HIS-tag fused to its N-terminus (expected size of the His EN protein is 29 kilodaltons, kDa). The right panel shows the Western blot analysis of 500 ng of CL and PE with the novel anti-human ORF2p monoclonal antibody. Molecular markers on the right, 10-250 kDa.

FIGS. 2A and B. FIGS. 2A and B show Western blot analyses of the specificity of the anti-human ORF2p monoclonal antibody in human cells. FIG. 2A. FIG. 2A shows an analysis of mouse and human ORF2 (predicted size 150 and 149 kDa, respectively) and EN (predicted size 30 and 26 kDa, respectively) proteins generated from expression plasmids containing codon-optimized human ORF2 (hORF2), a codon-optimized sequence corresponding to the human ORF2 endonuclease fragment (hEN), codon-optimized mouse ORF2 (mORF2) and a codon-optimized sequence corresponding to the mouse ORF2 endonuclease fragment (mEN) transiently transfected in 293 cells. The novel anti-human ORF2p monoclonal antibody specifically detects proteins of human origin. FIG. 2B. FIG. 2B shows Western blot analysis of the same samples as in FIG. 2A, performed with custom anti-mouse ORF2p polyclonal antibodies which specifically detect proteins of mouse origin. The control lane indicates cells that were transiently transfected with an empty vector. GAPDH was used as a loading control. The 15-150 kDa legend on the right indicate positions of molecular markers.

FIGS. 3A and B show the analysis of the expression of functional and non-functional human ORF2 protein in human cells. FIG. 3A. FIG. 3A shows the Western blot analysis of proteins generated from expression plasmids containing codon-optimized, functional ORF2 endonuclease sequence (EN) and non-functional ORF2 endonuclease sequence transiently transfected in HeLa cells. Western blot analysis was performed with anti-human ORF2p monoclonal antibody (top), anti-human ORF2p endonuclease polyclonal antibodies (middle), and anti-GAPDH antibodies (bottom). The non-functional ORF2 endonuclease sequence (EN 205, 230) has mutations resulting in expression of inactive ENp with D205A and H230A mutations. FIG. 3B shows the same experiment and analysis as in 3A, but using 293 cells. Western blot analysis of codon-optimized, non-functional ORF2 endonuclease sequences containing single inactivating mutations D205A or H230A (EN205 and EN 230, respectively) transiently transfected in 293 cells was performed using anti-human ORF2 monoclonal antibody (top), anti-human ORF2p endonuclease polyclonal antibodies (middle), or anti-GAPDH antibodies (bottom). Expected EN protein size is 26 kDa. Control lane indicates cells transiently transfected with an empty vector. Both Figures: the "25" or "37" to the right of each panel indicates the positions of molecular markers of 25 or of 37 kDa, respectively.

FIGS. 4A-E. FIGS. 4A-E show an analysis of expression of functional and non-functional full-length and truncated human ORF2 proteins in human cells. FIG. 4A. Schematic of L1 ORF2 protein. The following ORF2p domains are listed: Endonuclease domain (EN), Z domain (Z), Reverse Transcriptase domain (RT) and the Cysteine-Rich domain (Cys). Amino acid boundaries of each domain are listed. FIG. 4B. Western blot analysis of the full-length and truncated ORF2 proteins generated from expression plasmids containing codon-optimized, functional full-length ORF2 (ORF2) and C-terminally truncated ORF2 sequences transiently transfected in 293 cells with monoclonal antibody. Control lane indicates cells transiently transfected with an empty vector. FIG. 4C. Western blot analysis of proteins generated from expression plasmids containing codon-optimized mutant of the constructs described in A transiently transfected in 293 cells with monoclonal antibody. Constructs containing two inactivating mutations are labeled as 205, 230, and single mutants are labeled as 205 or 230. FIG. 4D. Western blot analysis of the same samples described in FIG. 4A with polyclonal anti-ORF2p antibodies. FIG. 4E. Western blot analysis of the same samples described in FIG. 4B with anti-human ORF2p polyclonal antibodies. FIGS. 4B-E: GAPDH is used as a loading control. Numbers to the right of each Figure indicate the kDa of molecular markers. Arrows on the left of each Figure denote bands of expected molecular weights for each construct listed FIG. 5.

FIGS. 6A and B show an analysis of the sensitivity of the novel anti-human ORF2p monoclonal antibody. FIG. 6A. Western blot analysis of protein generated from expression plasmids containing wild-type ORF2 endonuclease sequence (ENwt), codon-optimized ORF2 endonuclease sequence (ENco) and codon-optimized ORF2 sequence (ORF2) transiently transfected in 293 cells with the subject monoclonal antibody. Five or 10 micrograms (μg) of the whole cell lysate was used for analysis as indicated. Control lane indicates cells transiently transfected with an empty vector. Bacterially purified endonuclease was loaded at 0 (empty, buffer only), 10, 20, or 40 nanograms (ng). GAPDH was used as a loading control. The numerals to the right of the photo indicate positions of molecular markers of molecular weights shown in kDa. Arrows on the left denote bands of expected sizes for each protein. FIG. 6B is a graph showing a standard curve generated using the quantitation of the increasing amounts of the bacterially purified endonuclease shown in FIG. 6A. Signals detected for ORF2co, ENco and ENwt are plotted and labeled with the respective names of the proteins.

FIGS. 7A-C. FIGS. 7A-C show that the novel monoclonal anti-ORF2p antibody inhibits L1 endonuclease activity in an in vitro endonuclease cleavage assay. FIG. 7A. FIG. 7A is a schematic diagram of in vitro endonuclease cleavage assay. Double-stranded DNA containing L1 ORF2 endonuclease consensus target sequence has 5' tagged with fluorophore ("F"). L1 ORF2 endonuclease is added, and DNA is cleaved releasing the fluorophore, which can be quantitated. FIG. 7B. FIG. 7B, top panel, is a photo of an SDS-PAGE analysis of the products resulting from the in vitro endonuclease assay, with or without the addition of the monoclonal anti-ORF2 antibody (0 nm, or 100, 150, 200 nM, in the positions under the increasing bar). Antibody (ORF2) denotes the addition of the monoclonal anti-ORF2 antibody, control indicates the addition of the same volume of the buffer used for the reactions containing monoclonal anti-ORF2p antibody, and L1 EN denotes bacterially-purified human ORF2 endonuclease. FIG. 7B, bottom panel, is a graph showing quantitation of the results of the in vitro endonuclease cleavage assay in FIG. 7A. Results were normalized to 0 nM control (N=3). FIG. 7C. FIG. 7C shows the same experimental approach as in FIG. 7B, but anti-hORF1p antibody was added to the in vitro endonuclease cleavage assay.

FIG. 8 shows an analysis of the expression of functional and non-functional human ORF2 endonuclease domains in NIH-3T3 cells. Western blot analysis of proteins generated from expression plasmids containing codon-optimized functional (EN) and non-functional (EN 205,230) ORF2 endonuclease sequences transiently transfected in NIH-3T3 cells with anti-human ORF2p monoclonal antibody (top panel), anti-human ORF2p polyclonal antibodies (middle panel), or GAPDH (bottom panel). Control lane indicates cells transiently transfected with an empty vector. Numbers to the right of each panel show the molecular weights in kDa of molecular markers.

FIG. 9 shows an analysis of endogenous ORF2p in different cell lines. Top panel: The top panel shows a photograph of a Western blot analysis of total cell lysate from the following cell lines (labeled across the top of the photo): NIH-3T3, 293, Ntera2 and HeLa, using hybridoma supernatant. Protein lysate from 293 cells transiently transfected with an expression plasmid containing codon-optimized ORF2 was used as a positive control for ORF2p expression (third lane). "Control" lane indicates 293 cells transiently transfected with an empty vector. Numbers to the right of the panel show the molecular weights in kDa of molecular markers. Bottom panel: The same experiment and analysis as in the top panel, but using secondary antibodies only. Numbers to the right of the panel show the molecular weights in kDa of molecular markers. The total amount of cell lysate loaded in each lane is shown at the bottom in micrograms (μg).

FIG. 10 shows the photograph of an analysis of functional ORF2p endonuclease in native conformation. The right lane shows a Western blot analysis of the bacterially purified ORF2p endonuclease (EN) fractionated under native conditions using hybridoma supernatant. Buffer lane indicates storage buffer used for purified ORF2p endonuclease.

FIG. 11 presents a photo and a graph showing that the novel monoclonal anti-ORF2p antibody does not inhibit the APE1 endonuclease activity in vitro. Top panel: The top panel is a photograph of a SDS-PAGE analysis of in vitro APE1 endonuclease cleavage assay using monoclonal anti-ORF2 antibody. ORF2 antibody denotes the addition of 200 nM of the monoclonal anti-ORF2p antibody, "Control" indicates the addition of the same volume of the buffer used for the reactions containing monoclonal anti-ORF2 antibody, and "APE1" denotes bacterially-purified human APE1 endonuclease. Two concentrations of APE1, 0.1 and 0.01 units, were tested. Bottom panel: The bottom panel is a graph showing the quantitation of the results of the in vitro APE1 endonuclease cleavage assay in the top panel. Results were normalized to 0 nM control (N=3). The equation used to determine percent (%) inhibition is listed in the Examples.

FIG. 12 shows an analysis of ORF2p endonuclease conservation in human and mouse. Alignment of ORF2p endonucleases of L1Pa families in humans (SEQ ID NOS 7-14, respectively, in order of appearance) and the ORF2p endonuclease domain of mouse L1 Spa (SEQ ID NO: 15). Black arrow indicates area of the epitope of anti-ORF2p monoclonal antibody.

DETAILED DESCRIPTION

Introduction and Overview

Figure 1A:
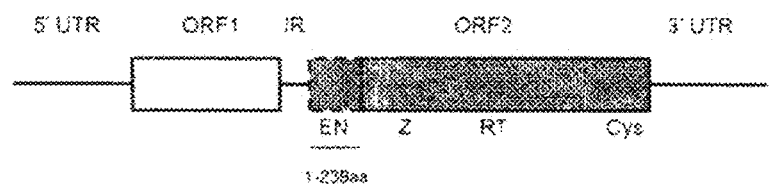
FIGS. 1A and B.

Long interspersed element-1 (also referred to as "LINE-1" and "L1") is the most common retrotransposon class in the human genome. Most L1 in the genome is not intact and is inactive. Active L1, however, can be a cause of genetic instability and has been associated with human disease. Babushok and Kazazian, Hum Mutat. 2007, 28:527-539. Kazazian et al, Nature, 1988, 332:164-166. L1 has two open reading frames, ORF1, and ORF2. ORF2 encodes a 150 kD protein, ORF2p, which has both endonuclease and reverse transcriptase activity.

Polyclonal antibodies to ORF2p have been available for some time. Despite the clear desirability of having monoclonal antibodies to ORF2p, and the efforts of others to develop such antibodies, none have been commercially available or reported in the literature. Without wishing to be bound by theory, it is believed that these efforts attempted to use the entire protein as the immunizing agent. Whatever the reason, the efforts were not successful in raising monoclonal antibodies that recognize the protein.

We now report the successful development of an antibody that specifically binds the endonuclease domain of L1 ORFp2. As shown by the studies reported in the Examples, the antibody, referred to herein as "monoclonal anti-human ORF2 endonuclease antibody" or "anti-hORF2 239," has a number of surprising properties. First, the antibody binds to the human, but not the mouse, ORF2p endonuclease ("EN") domain, despite the relatively strong sequence conservation between the endonuclease domains of the two proteins. Second, it binds ORF2p EN domain which is functional, but not ORF2p EN domain that is inactive due to a mutation at amino acid 205, a mutation commonly used to produce non-functional ORF2p endonuclease. Third, surprisingly, the antibody inhibits the activity of ORF2p endonuclease by about 25%. Fourth, and perhaps most surprisingly, the antibody inhibits the activity of ORF2p endonuclease without also inhibiting the in vitro activity of human apurinic/apyrimidinic endonuclease (human "APE1"), which is involved in the repair of DNA damage by the base excision repair pathway, despite the fact that APE1 shares sequence homology with the L1-encoded endonuclease. None of these properties could have been predicted, but their combination makes the antibody surprisingly advantageous. Further, since none of these advantageous properties depend on the presence of the constant, or "Fc," region of the antibody, these advantageous properties are also expected be possessed by fragments of the antibody, such as Fabs, F(ab)$_2$, Fvs, scFvs, which lack the Fc region but which retain the ability to specifically bind the L1 ORF2p endonuclease domain. The hybridoma secreting the antibody referred to herein as "monoclonal anti-human ORF2 endonuclease antibody" or "anti-hORF2 239," was deposited with the American Type Culture Collection (ATCC), 10801 University Boulevard, Manassas, Va. 20110, under the terms of the Budapest Treaty on Jun. 12, 2019, and has been assigned Name Designation 1G4E11 and Patent Deposit Number PTA-126005.

Monoclonal anti-human ORF2 endonuclease antibody and its antigen-binding fragments and derivatives have a number of uses. Their ability to bind functional human ORF2p endonuclease, but not ORF2p EN which is non-functional due to a mutation at position 205, makes them not only a useful laboratory reagent but also useful for detecting the presence of active ORF2p EN in patient samples. Detection of the presence of active ORFp2 EN informs the practitioner that genetic instability may be a contributing factor to the patient's condition. Their ability to inhibit human ORF2p endonuclease activity also makes them useful reagents for dissecting the effect of the endonuclease in genetic instability. Further, their ability to inhibit human ORF2p endonuclease activity without affecting the activity of human APE1, makes them useful in studying whether the reduction of ORF2 EN activity in conditions associated with L1-related genetic instability affects the viability or growth of cells in vitro and in animal models in which human cells have been implanted, as well as in reducing the effect of L1-mediated genetic instability in individuals suffering from a condition caused or aggravated by active L1.

Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. Definitions of common terms in molecular biology may be found in "Lewin's Genes XI", Krebs, J., et al., eds. (Jones & Bartlett Learning, Burlington, Mass., 2014); Kendrew et al. (eds.), The Encyclopedia of Molecular Biology, published by Blackwell Science Ltd., 1994; and Robert A. Meyers (ed.), Molecular Biology and Biotechnology: a Comprehensive Desk Reference, VCH Publishers, Inc., 1995. The headings provided herein are not limitations of the various aspects or embodiments of the invention, which can be had by reference to the specification as a whole. Accordingly, the terms defined immediately below are more fully defined by reference to the specification in its entirety.

An antibody is a polypeptide ligand comprising at least a light chain or heavy chain immunoglobulin variable region which specifically recognizes and binds an epitope of an antigen, such as L1, or a fragment thereof. Antibodies are composed of a heavy and a light chain, each of which has a variable region, termed the variable heavy ($V_H$) region and the variable light ($V_L$) region. In a natural antibody, the heavy and light chains are interconnected by disulfide bonds. Together, the $V_H$ region and the $V_L$ region are responsible for binding the antigen recognized by the antibody. For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, and antibody mimics, unless otherwise required by context.

References to "long interspersed element-1," "LINE-1," "L-1" and "L1" all refer to a member of a class of non-long terminal repeat retrotransposons that are the only active class of retroelements in the human genome. Singer, et al., Trends Neurosci. 2010, 33(8): 345-354. L1 is the most common retrotransposon class and comprises about 17% of the human genome. Belgnaoui et al., Cancer Cell Int., 2006, 6:13. L1 has two open reading frames ("ORFs"). ORF1 encodes a 40 kDa (p40) protein ("ORF1p") with RNA-binding activity, and ORF2 encodes ORF2p, a 150 kDa protein with endonuclease and reverse transcriptase activities.

References to "monoclonal anti-human ORF2p endonuclease domain" antibody or "hORF2 239" refer to a monoclonal antibody that binds to a L1 ORF2 protein endonuclease domain which does not have a mutation at position 205 (specifically, mutation D205A) that renders the endonuclease inactive.

References to a "binding reagent" which binds the endonuclease domain of human L1 ORF2 protein refers to monoclonal anti-human ORF2p endonuclease domain antibody or to fragments or derivatives of that antibody that bind to the endonuclease domain of human L1 ORF2 protein which does not have a mutation at position 205 (specifically, D205A) that renders the endonuclease inactive.

References to the "binding" of an antibody or fragment or derivative thereof to an antigen, such as L1 ORF2 protein endonuclease domain, refers to the formation of multiple noncovalent bonds between the antigen and the amino acids of the binding site responsible for the specificity and affinity of the antibody-antigen interaction.

References to "HORF2 hybridoma" refers to the hybridoma producing the hORF2 239 monoclonal antibody referred to in the previous paragraph.

The term "antibody fragments" means molecules that comprise a portion of an intact antibody, generally the antigen binding or variable region of the intact antibody.

Examples of antibody fragments include Fab ("fragment antigen binding"), Fab', F(ab')$_2$, and Fv ("fragment variable") fragments; helix-stabilized antibodies (see, e.g., Arndt et al., J Mol Biol 312:221-228 (2001); diabodies (see below); single-chain Fvs ("scFvs," see, e.g., U.S. Pat. No. 5,888,773); disulfide stabilized antibodies ("dsFvs", see, e.g., U.S. Pat. Nos. 5,747,654 and 6,558,672), domain antibodies ("dAbs," see, e.g., Holt et al., Trends Biotech 21(11):484-490 (2003), Ghahroudi et al., FEBS Lett. 414: 521-526 (1997), Lauwereys et al., EMBO J 17:3512-3520 (1998), Reiter et al., J. Mol. Biol. 290:685-698 (1999), Davies and Riechmann, Biotechnology, 13:475-479 (2001)) and "minibodies" (see, U.S. Pat. No. 5,837,821 and Hu et al., Cancer Res., 1996, 56:3055). In preferred embodiments, these fragments retain the ability to specifically bind ORF2p endonuclease domain.

References to "derivatives" of monoclonal anti-human L1 ORFp2 endonuclease domain antibody refers to chimeric or humanized forms of the antibody. In preferred embodiments, these derivatives retain the ability to specifically bind ORF2p endonuclease domain.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., Sequences of Proteins of Immunological Interest, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. (Other abbreviations are also employed which likewise designate the respective chain and CDR number of a particular CDR, such as CDR-L2 or H3-CDR. It is expected that persons of skill are familiar with these various designations for the six antibody CDRs.) The hORF2p 239 antibody has a specific $V_H$ region and a specific $V_L$ region sequence, and thus six specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues ("SDRs").

A "monoclonal antibody" is typically made by fusing myeloma cells with the spleen cells from a mouse that has been immunized with a chosen antigen. A cell which produces an antibody with the desired specificity and affinity is then grown to provide a clone of cells which produce the selected antibody. Monoclonal antibodies include humanized monoclonal antibodies.

A "chimeric antibody" has framework residues from one species, such as human, and CDRs (which generally confer antigen binding) from another species, such as a murine antibody that specifically binds L1 ORF2p.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

The term "diabodies" refers to small antibody fragments with two antigen-binding sites, which fragments comprise a variable heavy domain ("$V_H$" or "VH") connected to a variable light domain ("$V_L$" or "VL") in the same polypeptide chain ($V_H$-$V_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Hollinger et al., Proc. Natl. Acad. Sci. USA, 90: 6444-6448 (1993).

Certain organisms produce single chain antibodies. These organisms include the camelids (such as llamas), which produce antibodies composed of only two heavy chains, called heavy chain antibody (HCAb). Single domain antibodies, also known as "sdAbs" or "nanobodies," contain only the variable region of HCAb. The single variable domain antibodies, called "VHH," have a molecular weight of about 13 kD, are fully functional target binding fragments, and are useful both for their small size and for their stability. The structural features of such antibody fragments are known. See, e.g., Lopez Cardozo et al., "Single Domain Camelid Antibodies that Neutralize Negative Strand Viruses," in Arbuthnot, ed., Antiviral Drugs—Aspects of Clinical Use and Recent Advances, 2012 (InTech, Rijeka, Croatia, ISBN 978-953-51-0256-4). Sharks also produce heavy chain only, single domain antibodies, which are referred to as VNAR. See, e.g., Hamers-Casterman C et al., Nature, 1993, 363(6428):446-448; Muyldermans, Annu Rev Biochem., 2013, 82:775-797; Holliger and Hudson, Nat Biotechnol., 2005, 23(9):1126-1136, Wesolowski et al., Med Microbiol Immunol., 2009, 198(3):157-74; Saerens et al., Curr Opin Pharmacol., 2008, 8(5):600-608. In some embodiments, the present invention encompasses such $V_H$H fragments, nanobodies, and VNAR to the extent they comprise three CDRs of the anti-L1 ORF2p endonuclease domain monoclonal antibody described herein. In some embodiments, the three CDRs are the three CDRs of the heavy chain of the anti-L1 ORF2p endonuclease domain monoclonal antibody.

For numbering amino acid residues of antibodies for preparation of disulfide stabilized antibodies, references to amino acid positions of the heavy or light chains refer to the numbering of the amino acids under the Kabat system, described above. Since the numbering of a residue under the Kabat system aligns it to other antibodies to permit determination of the residues in the framework regions and the CDRs, the number assigned to a residue under the system does not necessarily correspond to the number that one might obtain for a residue in a given heavy or light chain by simply counting from the amino terminus of that chain. Thus, the position of an amino acid residue in a particular $V_H$ or $V_L$ sequence does not refer to the number of amino acids in a particular sequence, but rather refers to the position as designated with reference to the Kabat numbering scheme. There are other methods for numbering residues in the heavy and light chains. After Kabat, the most commonly used system is the Clothia system, which is the same as the Kabat system, except for placing the insertions in CDR-L1 and CDR-H1 at the structurally correct positions, which is considered to provide topologically equivalent residues in these loops do get the same label. Persons of skill in the art are familiar with the numbering of residues under both systems. See also, Martin, Andrew C. R., "Protein Sequence and Structure Analysis of Antibody Variable Domains," in: Kontermann and Durbel, eds., Antibody Engineering (Springer Heidelberg Dortrecht, London, $2^{nd}$ Ed. 2010, vol. 2). (Both volumes of Antibody Engineering are hereby incorporated by reference).

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

A "targeting moiety" or "targeting portion" is the portion of an immunoconjugate intended to target the immunoconjugate to a cell of interest. Typically, the targeting moiety is an antibody, or a fragment of an antibody that retains antigen recognition capability, such as a scFv, a dsFv, an Fab, or an F(ab')$_2$.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond.

The phrase "disulfide stabilized Fv" or "dsFv" refer to the variable region of an immunoglobulin in which there is a disulfide bond between the light chain and the heavy chain. In the context of this invention, the cysteines which form the disulfide bond are within the framework regions of the antibody chains and serve to stabilize the conformation of the antibody. Typically, the antibody is engineered to introduce cysteines in the framework region at positions where the substitution will not interfere with antigen binding.

Conservative variants: "Conservative" amino acid substitutions are those substitutions that do not substantially affect or decrease the affinity of an antibody to L1 ORF2p endonuclease domain. For example, a human antibody that specifically binds L1 ORF2p can include 1, at most about 2, at most about 5, at most about 10, or at most about 15 conservative substitutions and specifically bind the original L1 ORF2p endonuclease domain.

The term conservative variation also includes the use of a substituted amino acid in place of an unsubstituted parent amino acid, provided that antibody specifically binds L1 ORF2p endonuclease domain. Non-conservative substitutions are those that reduce binding to L1 ORF2p endonuclease domain or the ability to inhibit endonuclease activity.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

The term "immunoconjugate" includes reference to a covalent linkage of an effector molecule to an antibody.

Detecting (or detection): Refers to quantitatively or qualitatively determining the presence of a biomolecule under investigation.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "contacting" includes reference to placement in direct physical association.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. "Chemical means" refers to a reaction between the antibody moiety and the effector molecule such that there is a covalent bond formed between the two molecules to form one molecule, while "recombinant means" refers to expression of a nucleic acid resulting in production of a single, fusion protein which did not first exist as two separate molecules.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label can be a detectable marker, such as incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Proc. Nat'l Acad. Sci. USA 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 80%, and more preferably 90-95% or even higher nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, still more preferably over at least about 150 residues and most preferably over the full length of the sequence. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available on-line through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. (See Henikoff & Henikoff, Proc. Natl. Acad Sci. USA 89:10915 (1989)). In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively binds" refers, with respect to an antigen, the preferential binding of an antibody or antigen-binding fragment or derivative thereof, with a cell, cell lysate or other sample bearing that antigen and not to cells, cell lysates or samples lacking that antigen. It is recognized that a certain degree of non-specific interaction may occur between a molecule and a non-target cell or sample. Nevertheless, selective binding may be distinguished as mediated through specific recognition of the antigen. Although selectively binding antibodies bind antigen, they may do so with low affinity. On the other hand, specific binding results in a much stronger association between the antibody and samples containing the antigen than between the bound antibody and samples lacking the antigen. Specific binding typically results in greater than 2-fold, preferably greater than 5-fold, more preferably greater than 10-fold and most preferably greater than 100-fold increase in amount (per unit time) of bound antibody or fragment or derivative thereof to a sample, such as a cell or cell lysate, containing L1 ORF2p endonuclease domain as compared to a sample, such as a cell or cell lysate, lacking L1 ORF2p endonuclease domain. Specific binding to a protein under such conditions requires an antibody, fragment or derivative that is selected for its specificity for a particular protein. A variety of immunoassay formats are appropriate for determining the selectivity of antibodies that specifically bind a particular protein. For example, solid-phase ELISA immunoassays are routinely used to select monoclonal antibodies specifically immunoreactive with a protein. Harlow & Lane, ANTIBODIES, A LABORATORY MANUAL, Cold Spring Harbor Publications, New York (1988) ("Harlow & Lane"), and Greenfield, E. A., ed. ANTIBODIES, A LABORATORY MANUAL, SECOND EDITION, Cold Spring Harbor Publications, Cold Spring Harbor, N.Y. ($2^{nd}$ Ed., 2014) ("Greenfield") provide descriptions of immunoassay formats and conditions that can be used to determine specific immunoreactivity and antigen binding, as well as conditions under which a binding reagent, such as an antibody, antigen-binding fragment thereof, or antigen-binding derivative of an antibody, can bind to an antigen.

The term "immunologically reactive conditions" includes reference to conditions which allow an antibody generated to a particular epitope to bind to that epitope to a detectably greater degree than, and/or to the substantial exclusion of, binding to substantially all other epitopes Immunologically reactive conditions are dependent upon the format of the antibody binding reaction and typically are those utilized in immunoassay protocols or those conditions encountered in vivo. See Harlow & Lane, supra, and Greenfield, supra, for descriptions of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to more extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

LINE-1

References to "long interspersed element-1," "LINE-1," "L-1" and "L1" all refer to a member of a class of non-long terminal repeat retrotransposons that are the only active class of retroelements in the human genome. Singer, et al., Trends Neurosci. 2010, 33(8): 345-354. L1 is the most common retrotransposon class and comprises about 17% of the human genome. Lander et al., Nature 2001, 409(6822): 860-921. L1 has two open reading frames ("ORFs"). ORF1 encodes a 40 kDa (p40) protein with RNA-binding activity, while ORF2 encodes ORF2p, a 150 kDa, 1275 amino acid residue protein with endonuclease and reverse transcriptase activities. ORF2 was reported by Holmes et al., Nat. Genet., 1994, 7 (2), 143-148. The amino acid sequence of ORF2p is set forth in GenBank under accession number AAB60345.1. The GenBank annotation states that the endonuclease domain of the protein is from residue 10 to residue 237. As reviewed in Belgnaoui et al., Cancer Cell Int., 2006, 6:13, most of the L1 elements in the genome are not intact and are inactive; a small number, however, are retrotransposition-competent. Active L1 is considered a cause of genetic instability in the human genome and has been associated with human disease. Babushok and Kazazian, Hum Mutat. 2007, 28:527-539. Kazazian et al, Nature, 1988, 332:164-166. As persons of skill will appreciate, the various inactive forms of L1 differ from the sequence set forth under the GenBank accession number set forth above due to the mutations that inactivate them, and some of the active forms may have one or two mutations from the sequence set forth under the accession number that do not result in inactivating the encoded proteins.

Production of Monoclonal Antibodies, Humanization and Class Switching

The inventive monoclonal antibody was developed by immunizing mice with a fragment of the ORF2p containing the endonuclease domain, using standard protocols. Production of the monoclonal antibody of the present invention, however, proved not to be straightforward, as of the initial dozens of hybridomas produced, the only ones that were positive for binding the antigen bound bacterial LINE-1 ORF2p EN, but not ORF2p EN produced in human cells. A new set of mice had to be immunized and many more hybridomas made before one successfully produced a monoclonal antibody that bound human ORF2p EN.

The monoclonal anti-human ORF2p EN antibody and its fragments and derivatives are useful for in vitro applications. Rodent antibodies are immunogenic in humans and are rapidly removed from the circulation. In applications in which in vivo administration may be useful, it may therefore be desirable to reduce their immunogenicity by making chimeric forms or by humanizing the antibodies.

Methods of making chimeric antibodies by using human constant domains and mouse variable regions which retain binding specificity have been known for some thirty years, as exemplified by Boulianne et al., Nature, 1984, 312, 643-646 and Morrison et al., Proc. Natl. Acad. Sci. (USA), 1984, 81, 6851-6855. Other methods graft the CDRs of the murine antibody into human framework regions, resulting in a humanized antibody that preserves the specificity and binding affinity of the murine antibody while having significantly reduced immunogenicity compared to the parental, murine antibody. See, e.g., Jones, et al., Nature, 1986, 321, 522-525.

Methods of humanizing murine monoclonal antibodies have also been known in the art for many years, as exemplified by, Winter and Harris, "Humanized Antibodies," Trends Pharmacol Sci, 1993, 14(5):139-43. Replacement of the murine constant region with a human constant region has the greatest effect in reducing immunogenicity. E.g., Hwang and Foote, Methods. 2005, 36(1):3-10. A variety of methods are known in the art for humanizing antibodies, including framework-homology-based humanization, germline humanization, complementary determining regions (CDR)-homology-based humanization and specificity determining residues (SDR) grafting, as reviewed in Safdari et al., Biotechnol Genet Eng Rev., 2013, 29:175-86. Typically, the nucleic acid sequence of the antibody is determined and translated into the amino acid sequence. The amino acid residues in the murine constant region and in the variable region framework regions can then be compared to consensus sequences of the corresponding regions of human antibodies, with any differences in residues present at particular positions noted. A nucleic acid sequence can then be designed that results in changing residues in the murine antibody that differ from those of human antibodies at particular positions to the residue present in the human sequence.

A number of companies offer as a commercial service sequencing and humanization of murine monoclonal antibodies. Fusion Antibodies Ltd. (Belfast, Northern Ireland), for example, sequences mRNA extracted from hybridomas and provides a report on the consensus variable domains, including CDRs. It also combines the variable domains of provided antibodies, such as the murine inventive monoclonal anti-ORF2p antibody, with human antibody frameworks and constant domains to provide humanized versions of the antibodies. Similar services are available from Syd Labs, Inc. (Natick, Mass.). Alternatively, the amino acid sequence of the murine antibody can be determined and humanized antibodies produced using that sequence. LakePhama, Inc. (Belmont, Calif.), and GenScript (Piscataway, N.J.) for example, offer services including determination of the amino acid sequence of an antibody and providing humanized antibodies using the determined sequence. Humanized antibodies by CDR grafting is offered by Medical Research Council Technology (London, England), whose website (www[dot]antibodyengineering[dot]co[dot]uk) states that it has been providing humanized antibodies since 1987. Further, since determining the nucleic acid sequence of a monoclonal antibody is a commercial service, these companies can also provide the nucleic acid sequence of hORF2 239, which can then be used to express the antibody or a fragment of the antibody that retains antigen binding capability as a recombinant protein in bacterial or eukaryotic cells, using conventional techniques.

The inventive monoclonal antibody can similarly be switched to another isotype. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds ORF2p that was originally IgG may be class switched to an IgM. Class switching can also be used to convert one IgG subclass to another, such as from $IgG_1$ to $IgG_2$.

As noted, the CDRs of the anti-human L1 ORF2p endonuclease domain antibody can be humanized with a human framework region. Methods of providing human framework regions are known, as exemplified in U.S. Patent Publication No. US20120316085. See also PCT Publication No. WO 2006/074071.

Finally, as noted earlier, some active forms of L1 may have one or more mutations compared to the sequence set forth in the GenBank accession number set forth above. Given the specificity of the binding of the anti-L1 ORF2p endonuclease domain antibody to the EN domain, it is expected that antibodies and fragments containing the CDRs of the inventive anti-L1 ORF2p endonuclease domain antibody will specifically bind most forms of L1 with an active endonuclease domain.

Determinating CDRS in an Antibody

As noted in the preceding section, entities such as LakePharma, Inc. provide as a commercial service sequencing the amino acid sequence of any given antibody. In the case of non-human antibodies, such entities also offer to determine the CDRs and provide humanized versions of antibodies provided to them.

According to the bioinformatics group headed by Andrew Martin at the Bloomsbury Centre for Bioinformatics (London, England) on the website www[dot]bioinf[dot]org[dot]uk/abs/, the CDRs of an antibody can be determined positionally by looking at an amino acid sequence using the following guidelines:

CDR-L1: The CDR starts at approximately residue 24. The residue before the CDR is always a Cys, the residue after the CDR is always a Trp, and typically is the motif Trp-Tyr-Gln, but can also be: Trp-Leu-Gln, Trp-Phe-Gln, or Trp-Tyr-Leu, and has a length of 10 to 17 residues.

CDR-L2: The CDR start is always 16 residues after the end of CDR-L1, the residues before the CDR are generally Ile-Tyr, but can be Val-Tyr, Ile-Lys, or Ile-Phe, and the length is always 7 residues (except NEW (7FAB) which has a deletion in this region).

CDR-L3: The CDR start is always 33 residues after the end of CDR-L2 (except in NEW (7FAB) which has the deletion at the end of CDR-L2). The residue before the CDR is always Cys and the residues after the CDR are always Phe-Gly-XXX-Gly. The CDR has a length 7 to 11 residues.

CDR-H1: The start of the CDR is approximately residue 26, always 4 residues after a Cys (following the Chothia/AbM definition, the Kabat definition starts 5 residues later). The residues before the CDR are always Cys-XXX-XXX-XXX. The residue after is always a Trp, which is typically followed by a Val, but can be followed by an Ile or an Ala. The CDR has a length of 10 to 12 residues (AbM definition; the Chothia definition excludes the last 4 residues).

CDR-H2: The start of the CDR is always 15 residues after the end of (Kabat/AbM definition) of CDR-H1. The residues before are typically Leu-Glu-Trp-Ile-Gly (SEQ ID NO: 1), but there are a number of variations. The residues after the CDR can be Lys/Arg-Leu/Ile/Val/Phe/Thr/Ala-Thr/Ser/Ile/Ala. The length, under the Kabat definition, is 16 to 19 residues. The AbM (and Chothia) definition ends 7 residues earlier.

CDR-H3: The CDR start always 33 residues after the end of CDR-H2 (always 2 after a Cys). The residues before are always Cys-XXX-XXX (typically Cys-Ala-Arg); the residues after the CDR are always Trp-Gly-XXX-Gly. The length can be 3 to 25 residues.

Antibody Fragments

Antibody fragments are encompassed by the present disclosure, such as Fab, F(ab')$_2$, and Fvs which include a heavy chain and light chain variable region and are capable of binding the endonuclease domain of L1 ORF2p. These antibody fragments retain the ability to selectively bind with the antigen. These fragments include:

(1) Fab, the fragment which contains a monovalent antigen-binding fragment of an antibody molecule, which can be produced by digestion of a whole antibody with the enzyme papain to yield an intact light chain and a portion of one heavy chain;

(2) Fab', the fragment of an antibody molecule can be obtained by treating a whole antibody with pepsin, followed by reduction, to yield an intact light chain and a portion of the heavy chain; two Fab' fragments are obtained per antibody molecule;

(3) (Fab)$_2$, the fragment of an antibody that can be obtained by treating whole antibody with the enzyme pepsin without subsequent reduction; F(ab)$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (or "scFv"), defined as a genetically engineered molecule containing the variable region of the light chain and the variable region of the heavy chain, linked by a suitable polypeptide linker as a genetically fused single chain molecule; and, (6) A dimer of a single chain antibody (scFV$_2$), defined as a dimer of a scFV. This has also been termed a "miniantibody."

Methods of making these fragments are well known in the art (see for example, Harlow and Lane, supra, and Greenfield, supra).

In a further group of embodiments, the antibodies are Fv antibodies, which are typically about 25 kDa and contain a complete antigen-binding site with three CDRs per each heavy chain and each light chain. To produce these antibodies, the V$_H$ and the V$_L$ can be expressed from two individual nucleic acid constructs in a host cell. If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise V$_H$ and V$_L$ chains connected by a peptide linker. These single-chain antigen binding proteins (scFv) are prepared by constructing a structural gene comprising DNA sequences encoding the V$_H$ and V$_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are known in the art (see e.g., Whitlow et al., Methods: a Companion to Methods in Enzymology, Vol. 2, page 97, 1991; Bird et al., Science, 1988, 242:423-6; and U.S. Pat. No. 4,946,778). Dimers of a single chain antibody (scFV$_2$), are also contemplated. Pack et al., Bio/Technology, 1993, 11:1271-7, reported joining of two scFv fragments with a C-terminal hinge followed by a helix-turn-helix motif to form bivalent "miniantibodies" with a molecular weight "almost the same as that of a monovalent Fab."

Antibody fragments can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment (see, e.g., U.S. Pat. Nos. 4,036,945 and 4,331,647; Nisonhoff et al., Arch. Biochem. Biophys. 89:230 (1960); Porter, Biochem. J. 73:119 (1959); and Edelman et al., Methods in Enzymology, Vol. 1, page 422, Academic Press (1967)).

Uses of the Monoclonal Antibody, Fragments, and Derivatives

The monoclonal anti-ORF2p EN antibody and its fragments and derivatives can be used in vitro to detect human ORF2p EN that does not have an inactivating mutation at position 205. Further, as noted above, the monoclonal anti-ORF2p EN antibody and its fragments and derivatives inhibit the endonuclease activity of ORF2p. Accordingly, they can be used in in vitro studies to inhibit the endonuclease activity of ORF2p in cells from patients with pathological conditions. The practitioner can, for example, run parallel sets of cells from the patient, with a first set of cells being contacted with the monoclonal anti-ORF2p EN antibody or its fragments or derivatives, and a second set not being contacted with the monoclonal anti-ORF2p EN antibody or its fragments or derivatives, to determine whether downregulating ORF2p EN in the patient's cells has an effect on the viability or growth of the cells. Proteins can be efficiently delivered into cells by standard techniques, such as those reported in Weill et al., Cytotechnology. 2008 January; 56(1): 41-48 and Lee et al., Angewandte Chemie, 2010, 49(14):2552-2555. Further, human cells in which ORF2p EN is active can be grafted onto nude mice and monoclonal anti-ORF2p EN antibody or its fragments or derivatives can be administered to the mouse to determine how reducing genetic instability by downregulating ORF2p EN affects the viability or growth of a population of such cells.

In some embodiments, the antibody or a fragment or derivative thereof is conjugated to a detectable label, such as a radionuclide, a fluorescent moiety, or biotin, to facilitate detection of antibody or a fragment or derivative bound to ORF2p EN.

In some embodiments, monoclonal anti-ORF2p EN antibody or its fragments or derivatives can be administered to individuals having a condition associated with ORF2p EN activity by reducing genetic instability in the individual. As ORF2p is expressed intra-cellularly, the monoclonal anti-ORF2p EN antibody or its fragments or derivatives should be in a form that permits entry into cells. Typically, this can be accomplished by conjugating the monoclonal anti-ORF2p EN antibody or fragment or derivative thereof to a translocation domain of a toxin, such as Pseudomonas exotoxin A, by using a translocation adaptor sequence, or by using a variant of substance P to provide receptor-mediated delivery. Methods of delivering proteins and peptides into cells are reviewed in, e.g., Marschall et al., MAbs. 2011 January-February; 3(1): 3-16.

EXAMPLES

Example 1

This example sets forth materials and methods used in studies reported herein.

Cells

FLP-In™-293 (Invitrogen, Life Technologies Corp., Grand Island, N.Y.) cells were cultured in HyClone (GE Healthcare Life Sciences, Marlborough, Mass.) Dulbecco's modified Eagle's medium (DMEM) with 10% fetal bovine serum (Invitrogen) and maintained under 6% $CO_2$ at 37° C. HeLa (ATCC CCL2) cells, NIH-3T3 (ATCC CRL-1658) and Ntera2 (ATCC CRL-1973) cells were maintained as previously described (Perepelitsa-Belancio and Deininger, Nat Genet, 2003, 35(4):363-366).

Transfections

Western blot: 293 cells were seeded at $1.5 \times 10^6$ cells per T25 flask and transfected 16-18 hours later with 2 μg of the human or mouse ORF2 or EN expression plasmids (Kines et al., supra), or 1 μg, 2 μg or 4 μg of codon-optimized L1Pa1 (L1co, Wagstaff et al., PLoS ONE 2011, 6(5):e19672) or wild-type L1.3 (L1wt, Wei et al., supra; Wagstaff et al., supra). Plus reagent (6 μl) (Invitrogen) and Lipofectamine (8 μl) were used for each ORF2 or EN transfection reaction in serum-free media. 12 μl of plus reagent and 24 μl of Lipofectamine® (Thermo Fisher Scientific, Waltham, Mass.) were used for each transfection reaction with L1co or L1wt in serum-free media. Transfections with the maximum amount of the empty pCDNA plasmid were used as control. After three hours, serum-free media was replaced with serum-containing media, and the cells were harvested at 24 hours after transfection unless otherwise noted in the figure. HeLa and NIH-3T3 cells were seeded at $2 \times 10^6$ and $2.5 \times 10^6$ cells per T75 flask, respectively, and transfected as previously described (Sokolowski et al., PLoS ONE, 2013, 8(12): e82021) using 6 μg of plasmid, 12 μl of Plus reagent (Invitrogen) and 18 μl and 24 μl of Lipofectamine, respectively, were used in each transfection reaction in serum-free media.

Total Protein Extraction

Total protein was extracted as previously described (Kines, supra; Sokowlowski et al., supra) using phosphate buffered saline (137 mM NaCl (Sigma S9888), 2.7 mM KCl (Sigma P4505), 10 mM $Na_2HPO_4$ (Sigma S3264), 2 mM $KH_2PO_4$ (Sigma P9791), pH=7.4), 5 mM Ethylenediaminetetraacetic acid (EDTA, Sigma ED), and 0.02% Sodium Azide (Sigma S2002). Lysis buffer was supplemented with phosphatase inhibitors 2 and 3 (Sigma P5726, P0044 respectively) and Halt Protease inhibitors at 10 μl/mL each. The samples were subjected to two freeze (−80° C.)/thaw (25° C.) cycles. The samples were sonicated three times for 10 seconds at 12 watts RMS using a 3 mm wide QSonica Microson homogenizer with Microson ultra sonic disruptor XL2000 (Misonix). The protein concentration of each sample was determined using 595 nm wavelength OD values against a Bovine Serum Albumin (BSA) standard.

Western Blot Analysis

Ten μg-twenty μg of total protein were combined with 2× Laemmli buffer, 1.6 μl (14.3M) β-mercaptoethanol and boiled for 5 minutes prior to fractionation on Tris Acetate 3-8% Midi gels, Bis Tris 4-12% Midi gels (Invitrogen) and transferred onto nitrocellulose membranes (iBlot System; Invitrogen). Membranes containing fractionated protein samples were blocked for 1 hour in PBS-Tween containing 5% milk and incubated with a 1:250 dilution of custom polyclonal antibodies against the mouse ORF2p endonuclease, a 1:500 dilution of custom polyclonal antibodies against the human ORF2p endonuclease or a 1:250 dilution of custom monoclonal antibodies against the human ORF2p endonuclease overnight at 4° C. Detection was carried out using horseradish peroxidase-conjugated secondary antibodies of HRP-donkey anti-goat (Santa Cruz; sc-2020), HRP-donkey anti-rabbit (Santa Cruz; sc-2317), or HRP-goat anti-mouse (Santa Cruz; sc-2031) at a 1:5000 dilution in 3% milk in PBS-Tween for 1 hour. A 1:5000 dilution of GAPDH antibodies (Santa Cruz sc-25778) was used as an equal loading control. A HRP conjugated monoclonal antibody against the 6×HIS tag (SEQ ID NO: 2) (Pierce MA1-21315-HRP) was used at a 1:2000 dilution. All Western blots were developed using Clarity™ Western ECL Substrate (Bio-Rad, Cat. #170-5061).

Figure 5:
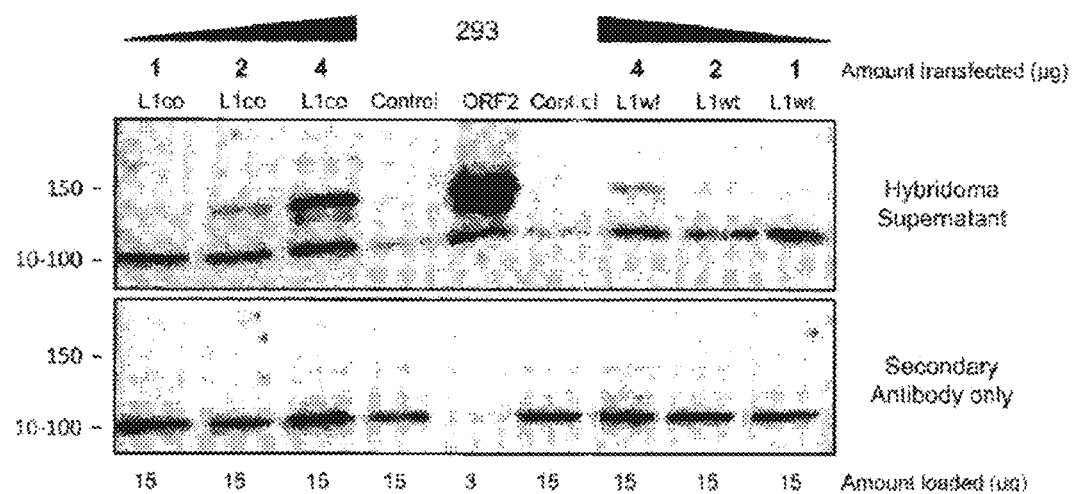
FIG. 5 shows an analysis of ORF2p generated from functional wild-type and functional codon-optimized full-length L1 expression plasmids in 293 cells. Top panel: Western blot analysis of ORF2p generated from expression plasmids containing a full-length wild-type L1 (L1wt), a full-length codon-optimized L1 (L1co) or a codon-optimized ORF2 transiently transfected in 293 cells with supernatant collected from cultured hybridoma cells producing anti-ORF2 antibody. 293 cells were transfected with 1, 2 or 4 micrograms (μg) of the L1wt or L1co expression plasmids or 2 micrograms of the ORF2 expression plasmid and total protein was harvested 24 hours after transfection. Control lane indicates cells transiently transfected with an empty vector. Positions of molecular markers are indicated on the left as 100 or 150 kDa. Bottom panel: The same experiment and analysis as in top panel, but using secondary antibodies only. Positions of molecular markers are indicated on the left as 100 or 150 kDa. Total amount of 293 cell lysate loaded is shown in micrograms (μg) at bottom of panel.

SDS Tris Glycine gels are shown in FIG. 5. Three μg-20 μg of total protein were combined with 2× Tris Glycine SDS sample buffer, 1.6 μl (14.3M) β-mercaptoethanol and boiled for 5 minutes prior to fractionation on Tris Glycine 4% Mini gels with Tris Glycine SDS running buffer (Invitrogen) and transferred onto nitrocellulose membranes (iBlot System; Invitrogen). Membranes containing fractionated proteins were blocked for 1 hour in PBS-Tween containing 5% milk at room temperature. The membranes were then incubated overnight at 4° C. with 1 mL of Ab-containing hybridoma supernatant in a blocking mixture containing 4 mL of media collected from NIH-3T3 cells cultured for 24 hours and 15 mL of 3% milk in PBS-Tween. Detection was carried out using horseradish peroxidase-conjugated secondary antibodies HRP-goat anti-mouse (Santa Cruz; sc-2031) at a 1:5000 dilution in 3% milk in PBS-Tween for 1 hour. All Western blots were developed using Clarity™ Western ECL Substrate (Bio-Rad, Cat. #170-5061).

One hundred ng of bacterially purified human ORF2p endonuclease was combined with 2× Native Tris Glycine sample buffer along with 5% GelCode Blue Stain Reagent (Thermo Scientific, Prod # 24592) and fractionated on a Tris Glycine 4-12% gel with Tris Glycine Native running buffer (Invitrogen). Fractionated proteins were transferred onto a nitrocellulose membrane (iBlot System; Invitrogen). Membranes containing fractionated proteins were blocked for 1 hour in PBS-Tween containing 5% milk at room temperature. The membranes were then incubated overnight at 4° C. with 1 mL of Ab-containing hybridoma supernatant in a blocking mixture containing 4 mL of media collected from NIH-3T3 cells cultured for 24 hours and 15 mL of 3% milk in PBS-Tween. Detection was carried out using horseradish peroxidase-conjugated secondary antibodies HRP-goat anti-mouse (Santa Cruz; sc-2031) at a 1:5000 dilution in 3% milk in PBS-Tween for 1 hour. All Western blots were developed using Clarity™ Western ECL Substrate (Bio-Rad, Cat. #170-5061).

Plasmids

All endonuclease constructs, ORF2 constructs, L1Pa1 (codon-optimized full-length L1) used are previously described in Kines et al., supra, and Wagstaffe et al., supra. 'L1wt' is JM101/L1.3 no tag (Wei et al., supra).

ORF2p Endonuclease Purification

A human ORF2 endonuclease was expressed in bacteria and the EN protein was purified as previously described (Repanas et al, supra; Nesterova et al., supra; Weichenrieder et al., Structure 2004, 12(6):975-986).

Monoclonal Antibody Production hORF2p endonuclease was bacterially purified as previously described (Repanas et al, supra; Nesterova et al., supra). This purified human ORF2 endonuclease protein was used for immunization of 6 Balb/c mice to generate monoclonal anti-ORF2p antibodies following standard immunization protocol. Briefly, three sequential immunizations (with two week intervals between the injections) with antigen, (purified ORF2p endonuclease diluted in saline) in complete Freund's adjuvant for the first injection and incomplete Freund's adjuvant for the second and third injection, injected intraperitoneally were performed. The fourth and final immunization was done using the antigen in saline. Mice were bled and tested using ELISA to determine which mouse to use as the source of B-cells for hybridoma production. Electrofusion was performed between B-cells harvested from the spleen and myeloma cells to produce hybridomas. Resulting hybridoma clones were screened with indirect ELISA to identify positive clones. The final stock of antibody was obtained by protein-G affinity column purification. The antibodies were stored in a PBS with 0.02% W/V sodium azide storage solution. The affinity purified hORF2p monoclonal antibodies were used for subsequent testing.

LINE-1 EN Cleavage Assay

LINE-1 EN was expressed and purified as described previously (Repanas et al, supra; Nesterova et al., supra). The LINE1 EN cleavage assay was performed using 200 nM purified LINE1 EN, 100 nM of a duplexed oligonucleotide containing LINE-1 EN target site. The reaction buffer contained 20 mM Hepes (pH 6.5), 150 mM NaCl, 1 mM $MgCl_2$, 1 mM dithiothreotol (DTT), 1% dimethyl sulfoxide (DMSO), 0.1% triton and 0.01% sodium azide. The effect of the monoclonal anti-ORF2p antibody on LINE1 EN activity was tested using three concentrations: 100 nM, 150 nM and 200 nM. The antibody was diluted into the above described reaction buffer just prior to use. The same was done for the anti-hORF1p antibody (Sokolowski et al., supra). A buffer control was used for background subtraction, in which the same volume of buffer alone as the volume of buffer containing antibody was added to the reactions. The LINE-1 EN and APE1 EN cleavage reactions were carried out at 37° C. for 30 minutes. The reactions were stopped by quenching on ice and the addition of stop solution: 1× Tris borate EDTA buffer, 80% formamide, 0.01 mM EDTA and xylene cyanol. The samples were run on 18% denaturing acrylamide gels and were analyzed using the Typhoon imager (GE Lifesciences). Fluorescense intensity (FI) was measured using Image Quant software (GE Lifesciences) and graphed using Prism software (GraphPad Software, Inc., La Jolla, Calif.). The percent inhibition of each reaction was determined using the following equation: % Inh=$100*(1-(FI_{Antibody}-FI_{Buffer\ Control})/(FI_{L1/APE1\ EN}-FI_{Buffer\ Control}))$.

Ape1 EN Cleavage Assay

Purified APE1 EN was purchased from New England Biolabs. The assay was performed using 0.01 and 0.1 units of enzyme and 200 nM of duplexed oligonucleotide containing an abasic site. The sequence of the oligonucleotide was based upon previously published work (Madhusudan et al., Nucl Acids Res, 2005, 33(15):4711-4724). The reaction buffer contained 50 mM potassium acetate, 20 mM tris-acetate, 10 mM magnesium acetate, 1 mM DTT, 1% DMSO, 0.1% triton and 0.01% sodium azide.

Annealing Oligonucleotides

All oligonucleotides were purchased from Integrated DNA Technologies. The oligonucleotides used in the assays were annealed by adding equivalent amounts of each complimentary nucleotide in annealing buffer (50 mM Hepes (pH 7.5) and 100 mM NaCl). The samples were incubated in boiling water for 5 minutes and slow cooled for 1 hour in the dark. The sequences for the LINE1 EN oligonucleotides used in the assay are as follows: 5'/AlexaFluor488/CCTTTTTTTTTAACCGC3' (SEQ ID NO: 3) and 5'GCGGTTAAAAAAAAAGG3' (SEQ ID NO: 4). The sequences for the APE1 EN oligonucleotides used in the assay are as follows: 5'/AlexaFluor488/GCCCCC_GGGGACGTAC-GATATCCCGCTCC3' (SEQ ID NO: 5) (where "_" represents an abasic site) and 5'GGAGCGGGATATCG-TACGTCCCCCGGGGGC3' (SEQ ID NO: 6).

Alignment of Human and Mouse ORF2p Endonuclease Domains

Human L1 Pa family consensus sequences (Khan et al., Genome Res, 2006, 16(1):78-87) and L1 Spa (Naas et al., EMBO J, 1998, 17(2):590-597) ORF2 sequence were converted to amino acid sequences and aligned using the DNASTAR MegAlign program (DNASTAR, Inc., Madison, Wis.) through the Clustal V method utilizing a gap penalty of '10' and a gap penalty length of '10'.

Calculation of the Number of Protein Molecules

The molecular weight of all proteins was calculated based on their amino acids composition using EditSeq software. The number of molecules detected by monoclonal anti-ORF2p antibody was calculated using the following formula:

$$X \text{ molecules} = [\text{Mass (g)/Molecular weight of a specific protein (g/mol)}] \times 6.022 \times 10^{23} \text{ (mol}^{-1}\text{)}.$$

Example 2

This Example sets forth the results of the studies reported herein.

Generation of Monoclonal Antibody Against Human L1 ORF2p Endonuclease

Figure 1B:
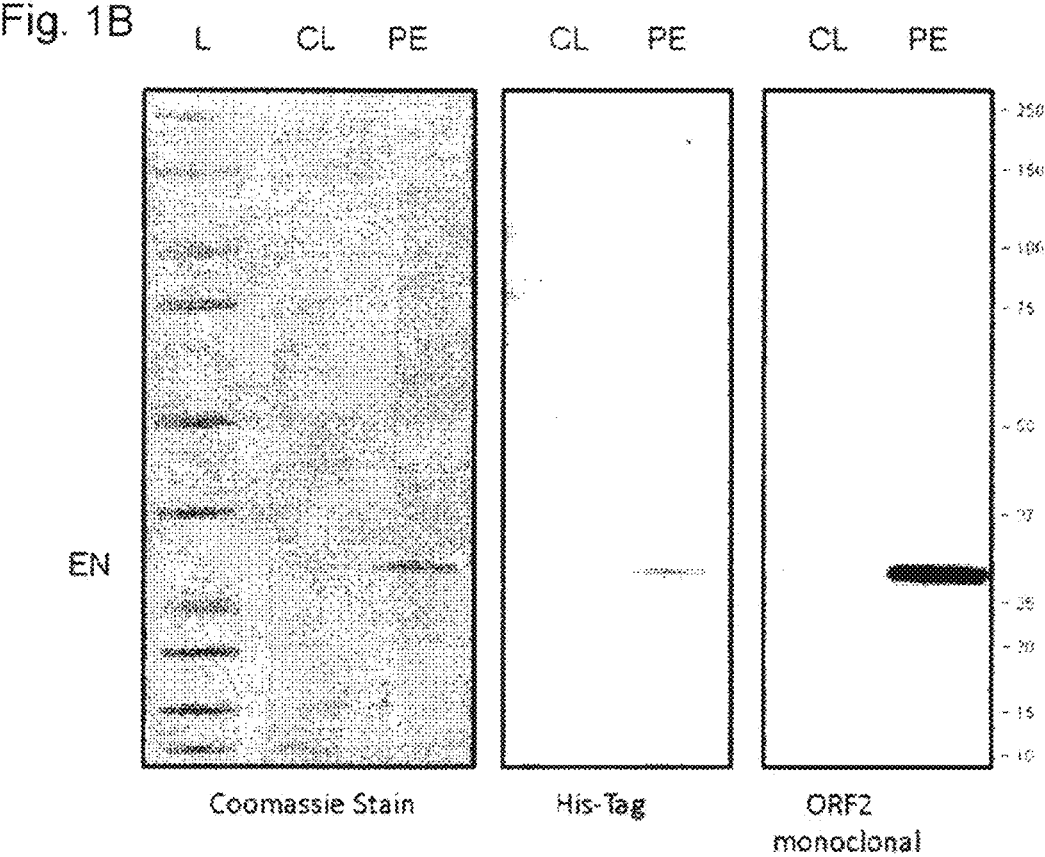
FIG. 1B.

A recombinant human protein containing an ORF2p EN domain N-terminally fused to a His-tag was purified from bacterial cells, subjected to SDS-PAGE and visualized using Coomassie stain. FIG. 1B shows the Coomassie panel with an expected product of 29 kDa. The efficiency of purification was also confirmed using antibodies against the His-tag fused to the N-terminus of the ORF2p EN, as seen in FIG. 1B, His-tag panel. This purified recombinant human EN protein was used for the immunization of Balb/c mice to generate monoclonal anti-ORF2p antibodies following a standard immunization protocol. This approach resulted in a positive hybridoma clone which was used to produce the purified anti-ORF2p monoclonal antibodies. Western blot analysis using this custom ORF2p monoclonal antibody detected a product of the expected size in the clarified lysate and the final elution of the human EN protein used for inoculation, as shown in FIG. 1B, ORF2 monoclonal panel.

Anti-ORF2p Monoclonal Antibody is Specific to the ORF2 Protein of Human Origin

The anti-ORF2p monoclonal antibody detects full-length ORF2p and ORF2p endonuclease in total cell lysates from 293 cells transiently transfected with plasmids containing human codon-optimized full-length ORF2 or the ORF2 endonuclease sequences, shown by FIG. 2A, lane hORF2 and hEN. Because the endonuclease domain of the L1 ORF2 protein is highly conserved between the human and mouse ORF2 proteins, whether the antibody discriminates between ORF2 proteins of human and mouse origin was tested. Plasmids encoding mouse codon-optimized full-length ORF2 or ORF2 endonuclease sequences were transiently transfected into 293 cells and total cellular lysates were analyzed by SDS-PAGE followed by immunoblotting with the anti-ORF2p monoclonal antibody. This approach determined that the anti-ORF2p monoclonal antibody does not detect mouse ORF2 or EN proteins (mORF2p and mENp, respectively) even though it detected both human ENp and ORF2p, shown in FIG. 2A, monoclonal Ab panel. The mouse ENp and ORF2p were detected by Western blot analysis performed with polyclonal antibodies raised against the endonuclease domain of the mouse ORF2p, seen in FIG. 2B, mouse Ab panel, confirming that the proteins are expressed under these transfection conditions.

Figure 3A:
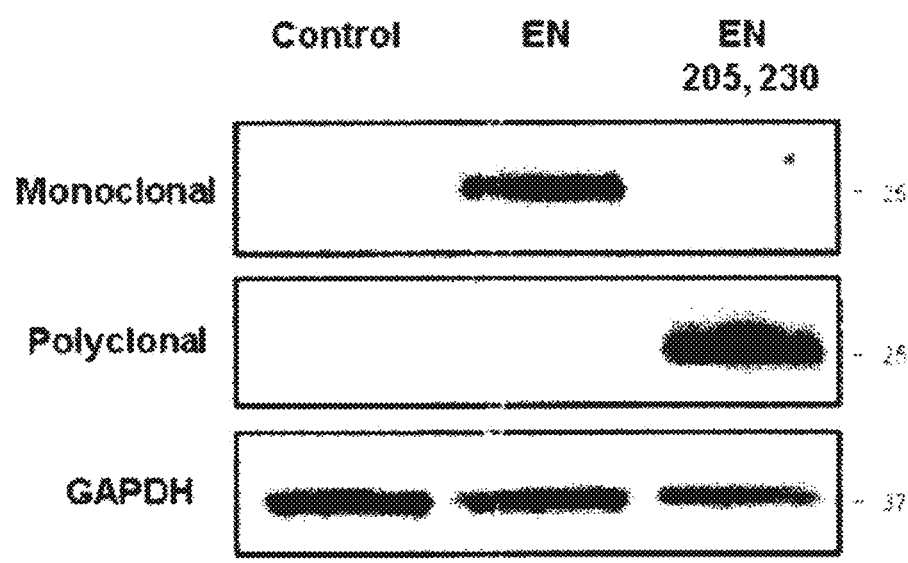
FIGS. 3A and B.
Figure 8:
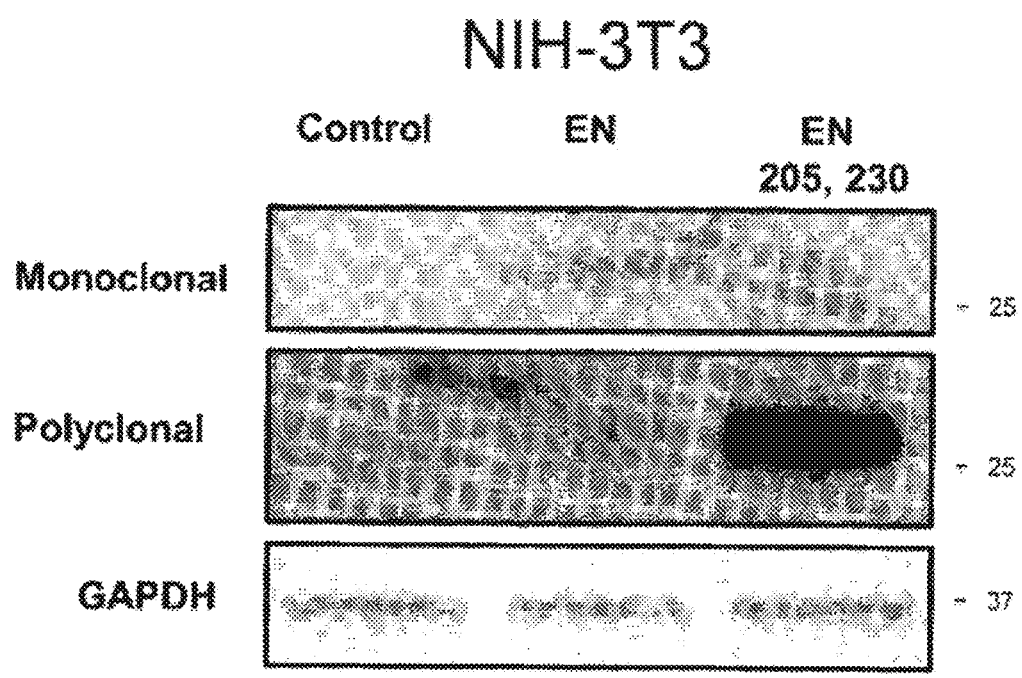
FIG. 8.
Figure 9:
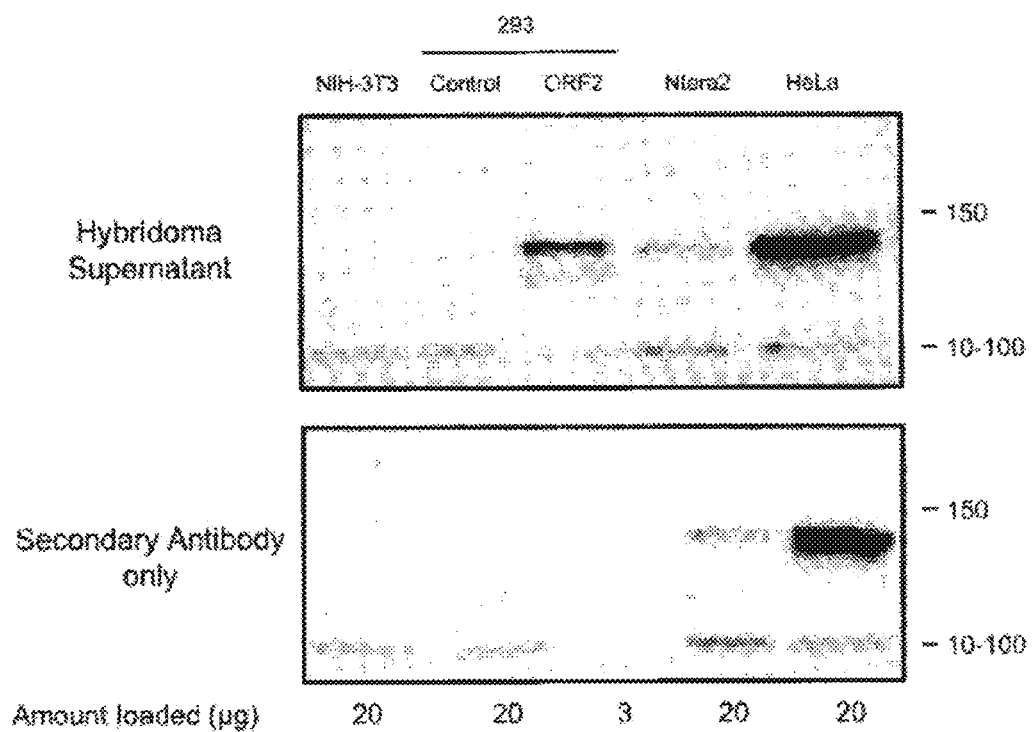
FIG. 9.

Anti-ORF2p Monoclonal Antibody Recognizes an Epitope which Includes Amino Acid 205 of the Human ORF2p Endonuclease Many experimental approaches designed to analyze the expression and function of ORF2p involve the use of both functional and non-functional ORF2 proteins. The most commonly used mutations, which abolish the activity of the ORF2p endonuclease, are D205A and H230A (Feng et al., supra, Morrish et al., Nat Genet, 2002, 31(2):159-165) Western blot analysis of total cellular lysates from human and mouse cells transiently transfected with EN or EN 205, 230 plasmids containing codon-optimized sequences producing functional or non-functional (D205A, H230A double mutant) human endonucleases demonstrated that the anti-ORF2p monoclonal antibody detects the active, but not the mutated, endonuclease protein. This is shown by FIG. 3A, monoclonal and FIG. 8, monoclonal. Both proteins were detected using the polyclonal anti-ORF2p antibody, also seen in FIG. 3A and FIG. 8.

Figure 3B:
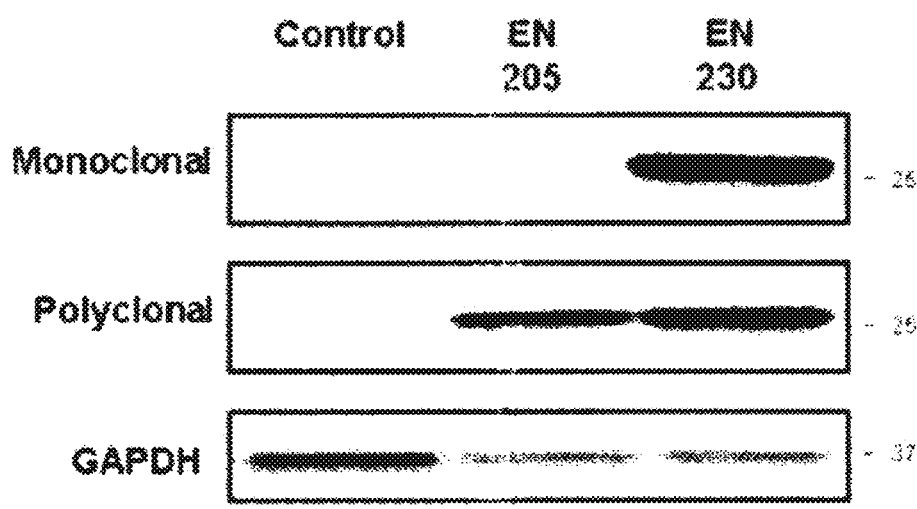
FIG. 3B.
Figure 4A:

To determine which EN mutation is responsible for the loss of detection by this anti-ORF2p monoclonal antibody, total cellular lysates from cells transiently transfected with EN 205 and EN 230 plasmids expressing non-functional endonuclease with D205A or H230A mutations were used for Western blot analysis with the anti-ORF2p monoclonal antibody, shown by FIG. 3B, monoclonal. This approach demonstrated that the anti-ORF2p monoclonal antibody detects ENp containing the H230A mutation but not the ENp with the D205A mutation, also shown by FIG. 3B, monoclonal. Both ENp mutants are readily detected with anti-ORF2p polyclonal antibodies, demonstrating that both proteins are produced under these transfection conditions, shown by FIG. 3B, polyclonal. A similar result was obtained when the monoclonal anti-ORF2p antibody was used to detect transiently expressed functional (ORF2) and non-functional (single and double mutants) full-length human ORF2 proteins (ORF2 205, ORF2 230, and ORF2 205,230, respectively), as well as truncated, functional and double mutant human ORF2 proteins (ENz and ENRT). Data is shown in FIG. 4A-E, ORF2, ENz, and ENRT. The anti-ORF2p monoclonal antibody specifically detected functional, but not non-functional, ENz, ENRT, and ORF2 proteins containing the D205A and H230A mutations, even though all of these proteins were produced in the cells, as confirmed by Western blot analysis using polyclonal anti-ORF2p antibodies, shown in FIG. 4D and FIG. 4E. These results demonstrate that the epitope recognized by the anti-ORF2p monoclonal antibody includes amino acid 205 of the human ORF2p endonuclease domain.

Sensitivity of the Anti-ORF2p Monoclonal Antibody

Figure 6A:
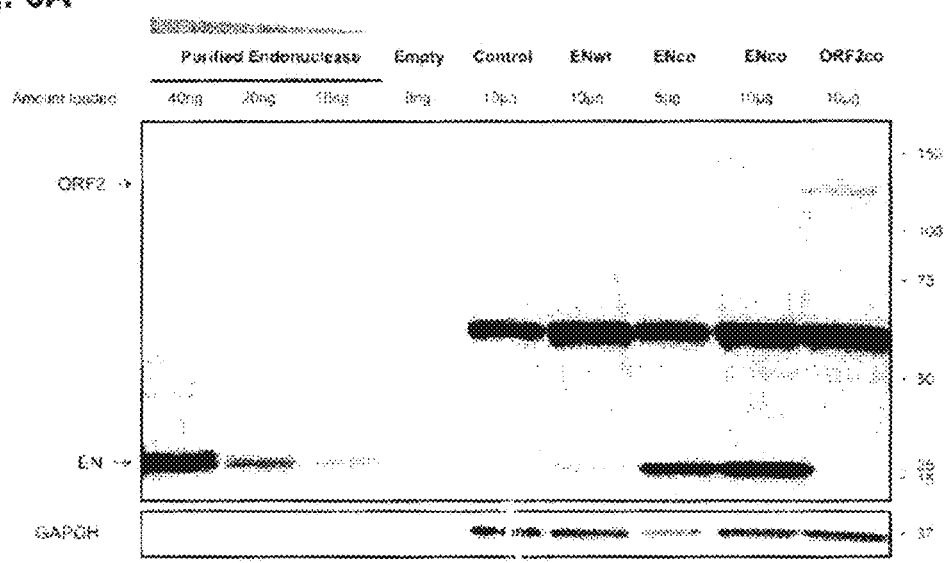
FIGS. 6A and B.
Figure 6B:
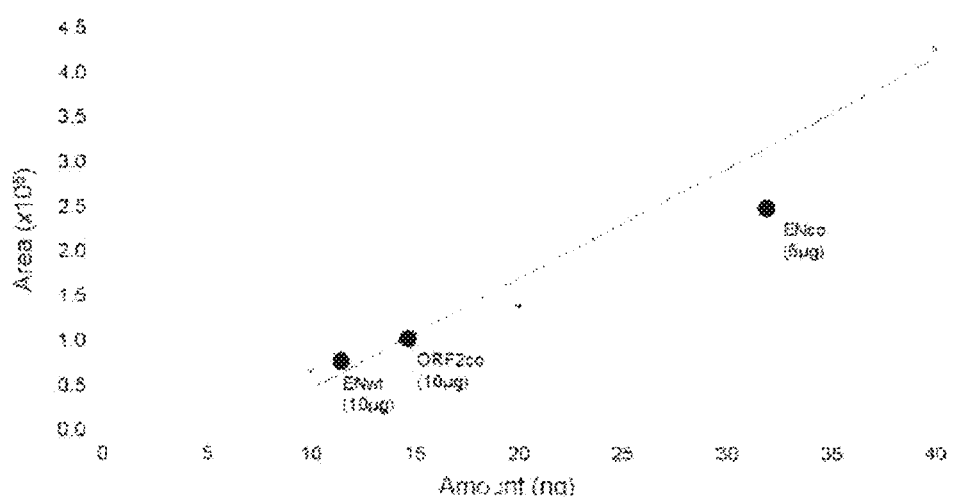
FIG. 6B.

The advent of L1 expression plasmids containing codon-optimized sequences facilitated our ability to detect L1-encoded proteins in transfected mammalian cells (Han and Boeke, Nature, 2004, 429(6989):314-318; Wagstaff, supra). However, it remains important to study L1 proteins generated from wild-type L1 sequences and to understand the difference in expression levels between proteins generated from codon-optimized and wild-type L1 sequences. As with the wild-type full-length L1 and ORF2 expression plasmids, codon-optimized full-length L1 expression plasmids produce much less ORF2 protein than those containing codon-optimized ORF2 sequence (Taylor et al., Cell, 2013, 155 (5):1034-1048; Alisch et al., Genes & Devel, 2006, 20(2): 210-224). Consistent with this fact, the anti-ORF2p monoclonal antibody detected different levels of ORF2p in cells transfected under the same conditions with L1 expression plasmids containing wild-type or codon-optimized sequences, as shown by FIG. 5. Transient transfection of 293 cells with plasmids containing codon-optimized ORF2 or full-length wild-type L1 sequences produced the highest and the lowest levels of ORF2 protein, respectively. Transfection of increasing amounts of plasmids containing codon-optimized or wild-type full-length L1 sequences demonstrated that detectable levels of ORF2p were observed when 2 μg and 4 μg of the respective plasmids were used. Using the recombinant human endonuclease purified from bacterial cells as a standard, it was determined that 27.6 μg of the anti-ORF2p monoclonal antibody is able to detect 10 ng ($2.2 \times 10^{17}$ molecules) of the purified hEN under these blotting conditions, seen in FIG. 6A. Based on the standard curve generated by Western blot analysis of the recombinant human EN purified from bacterial cells, it was determined that transfection of expression plasmids containing codon-optimized (co) human L1 sequences produce 5-6 times more endonuclease protein than that observed from cells transfected with equivalent amounts of plasmids containing wild-type sequences. Data is shown in FIG. 6, ENwt and ENco.

Figure 7A:
Figure 10:
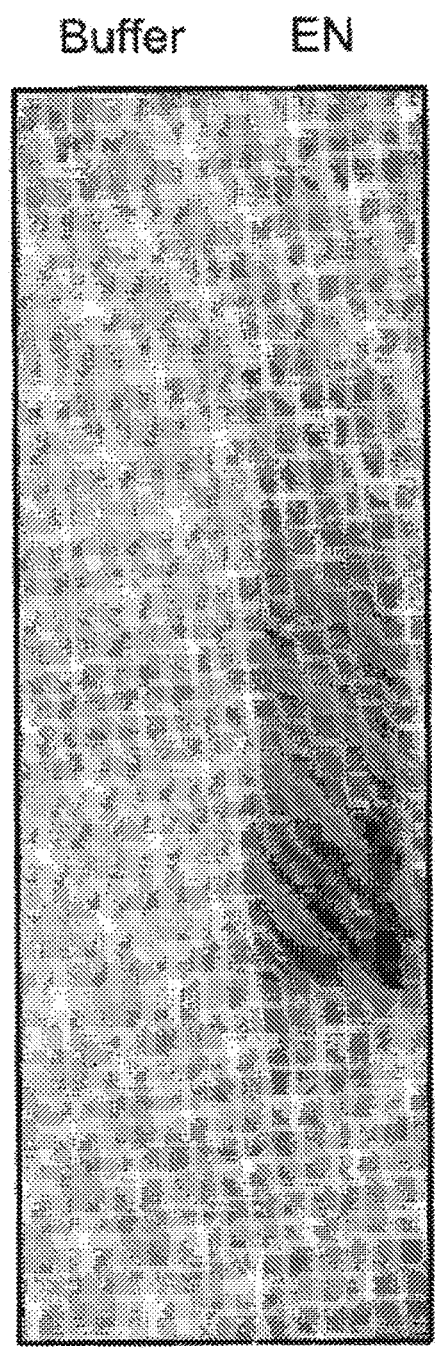
FIG. 10.

Monoclonal Anti-ORF2p Antibody Inhibits L1 Endonuclease Activity in an In Vitro Endonuclease Cleavage Assay The unique epitope location within the L1 EN, as well as the antibody's ability to detect natively folded ORF2p endonuclease purified from bacterial cells, shown in FIG. 10, indicate that the monoclonal antibody inhibits L1 endonuclease activity. For this purpose, a previously reported in vitro endonuclease cleavage assay was used to measure L1 EN activity (Repanas, supra, Nesterova, supra). FIG. 7A shows a schematic of the DNA products expected to be observed upon cleavage of the substrate DNA by the L1 EN at the L1 EN site present in the template DNA sequence. FIG. 7B demonstrates detection of the expected cleavage products resolved by PAGE when a bacterially purified, functional human L1 EN protein is present in the reaction. The addition of increasing amounts of the monoclonal anti-ORF2p antibody resulted in about 25% reduction of the cleaved products, seen in FIG. 7B. This effect was not observed when an unrelated, anti-ORF1p antibody was included in the reaction, as shown in FIG. 7C. A similar in vitro endonuclease cleavage assay using a functionally-related recombinant human apurinic/apyrimidinic endonuclease 1 (APE 1), which shares sequence homology with the L1-encoded endonuclease, was used to test the specificity of this effect. There was no observed change in the APE 1 activity upon the addition of the highest amount of the L1 EN-specific antibody of 200 nM, shown by FIG. 11.

Example 3

This Example discussed the results of the studies reported herein.

L1 is responsible for all of the retrotransposon-induced genomic instability in the human genome, as it is the only active source of the functional ORF1 and ORF2 proteins required for mobilization of LINEs, SINEs, and SVA elements (Gasior et al., J Molec Biol, 2006, 357(5):1383-1393; Robberecht et al., Genome Res, 2013, 23(3):411-418; Dombroski et al., Science, 1991, 254:1805-1808; Han et al., Proc Natl Acad Sci (USA), 2008, 105(49):19366-19371; Mild et al., Cancer Res, 1992, 52(3):643-645; Pickeral et al., Genome Res, 2000, 10(4):411-415). L1 expression and retrotransposition are suppressed by many diverse cellular pathways, in order to minimize the genomic damage inflicted by L1 activity (Taylor, supra; Zhang et al., Nucl Acids Res, 2014, 42(6):3803-3820; Yang and Kazazian, Nat Struct Mol Biol, 2006, 13(9):763-771; Goodier et al., Nucl Acids Res, 2013, 41(15):7401-19; Horn et al., Nucl Acids Res, 2014, 42(1):396-416, Belancio et al., Nucl Acids Res, 2006, 34(5):1512-1521; Bogerd et al., Proc Natl Acad Sci (USA), 2006, 103(23):8780-8785; de Haro et al., Nucl Acids Res, 2014, 42(12):7694-7707; Perepelitsa-Belancio et al., Nat Genet, 2003, 35(4):363-366). L1 encodes an ORF2 protein with several identified functions essential for the retrotransposition process. These include the endonuclease and reverse transcriptase activities and a putative RNA binding domain within the C-terminus of the protein (Feng et al., supra, Xiong and Eickbush, supra; Piskareva et al., supra). Increasing the understanding of the biological relevance of this multifunctional protein and its effect on human health necessitates manipulations involving changes in protein sequence as well as characterization of the expression of resulting ORF2p variants in vitro, in cultured cells, and in vivo. To that end, polyclonal antibodies against the L1 ORF2 protein of mouse and human origin have been previously reported.

The present invention discloses novel monoclonal antibodies to the human L1 ORF2p endonuclease domain that will help to advance future studies involving ORF2p expression and function. The monoclonal nature of the antibody provides a continuous source of antibody, thereby eliminating the issue with reproducibility commonly associated with different batches of polyclonal antibodies raised against the same antigen. Similar to previously reported polyclonal antibodies, the present monoclonal anti-ORF2p antibody detects untagged ORF2 protein expressed from the plasmids containing full-length wild-type or codon-optimized L1 elements. This characteristic is beneficial because the addition of different tags can interfere with L1 protein function or subcellular localization (Taylor et al., supra; Sokolowski, et al., supra). Using bacterially purified endonuclease protein, a standard curve was generated, allowing for a determination of the sensitivity of the novel monoclonal antibodies. The sensitivity of the antibodies is about 10 ng of the purified protein under described detection conditions, as shown in FIG. 6. Consistent with previous reports, we confirmed that codon-optimization of the human L1 ORF2 sequence results in a 5-6-fold increase in the EN protein production. Endogenously expressed L1 ORF2p was unable to be detected in HeLa and 293 cells; calculations suggest that endogenous levels of L1 ORF2p expression are less than 10 ng of protein per 10 µg of cellular lysate.

Figure 12:
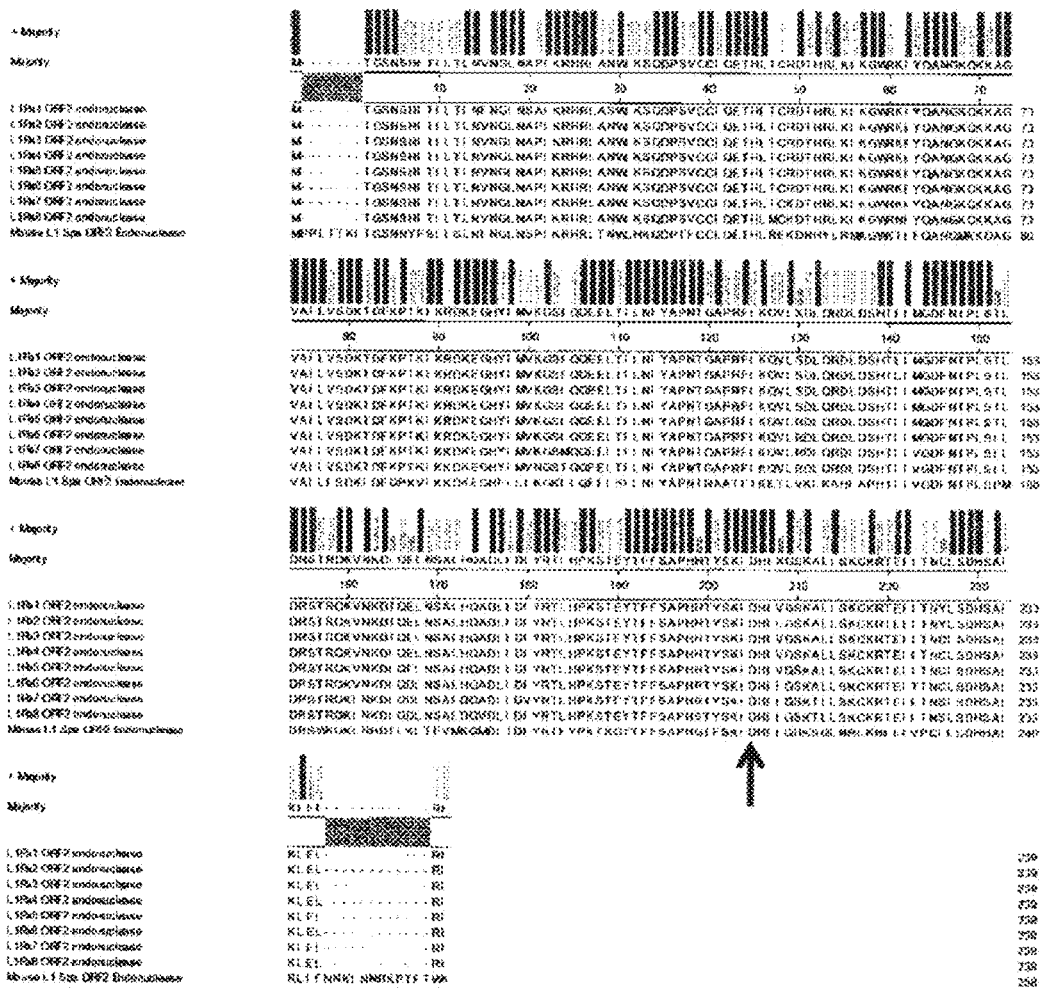
FIG. 12.

The results reported herein show that the anti-ORF2p monoclonal antibody specifically recognizes human, but not mouse, ORF2 protein, despite the relatively strong sequence conservation between the endonuclease domains of the two proteins, as seen in FIG. 12 (Wagstaff et al., supra; Khan et al., Genome Res, 2006, 16(1):78-87). This feature is useful for studies involving mouse cells and human ORF2 protein. The results also show that the epitope recognized by the monoclonal anti-ORF2p antibody includes amino acid 205 of the human ORF2p endonuclease domain. This amino acid is required for ORF2p endonuclease activity and is therefore necessary for L1-driven retrotransposition, shown by FIGS. 3 A and B and FIGS. 4B-E. As a result, the novel antibody exhibits some bias toward detection of the ORF2 proteins containing a functional endonuclease domain, at least relative to the status of amino acid 205. Additionally, an alignment of the consensus L1PA1-PA8 ORF2p sequences (Khan et al., supra) demonstrated that L1PA3-5 have the same sequence as L1 PAL L1PA 2, 6, and 7 have one substitution in the core region surrounding amino acid 205 (200-210aa), and L1PA8 varies by two amino acids from the L1PA1 sequence. See FIG. 12.

Figure 11:
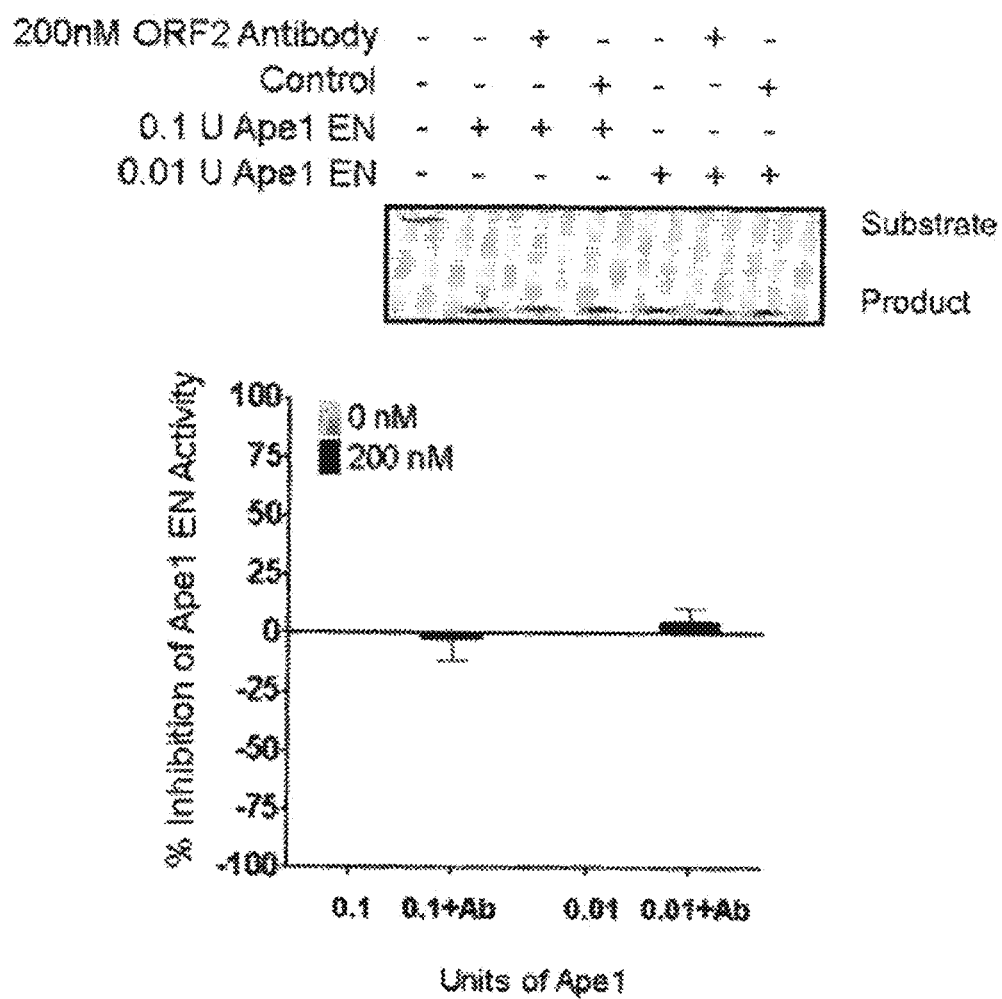
FIG. 11.

Taken together, the data shown that the present monoclonal antibody inhibits human L1 endonuclease activity. Suppression of L1 retrotransposition by HIV reverse transcriptase ("RT") inhibitors has been previously reported (Dai et al., BMC Biochemistry, 2011, 12(1):18; Kroutter et al., PLoS Genet, 2009, 5(4):e1000458), generating an interest in developing L1-specific inhibitors with the potential to suppress L1-associated damage in vivo. While the use of such RT inhibitors serves as a helpful tool to study the L1 replication cycle, these inhibitors are not specific to L1, as they are also expected to suppress telomerase RT (Strahl and Blackburn, Molecul. Cellular Biol, 1996, 16(1):53-65). Furthermore, they have significant side effects in humans (D'Andrea et al., Curr Clin Pharmacol, 2008, 3(1):20-37) and it is not known whether the inhibition of the reverse transcriptase also prevents damage from the L1 endonuclease-induced DNA double-stranded breaks (DSBs). In contrast, inhibition of L1 endonuclease activity is an attractive approach in order to suppress some, if not all, of L1-induced damage. Two of the main types of inhibitors generally used for the suppression of enzymatic activities are chemical inhibitors and antibody-based inhibitors. In addition to the effective inhibition of enzyme activity, efficient delivery, stability, and lack of toxicity are common goals for both types of inhibitors (Imai and Takaoka, Nat Rev Cancer 2006, 6(9):714-727; Hidalgo and Eckhardt, J Natl Cancer Inst, 2001, 93(3):178-193). The specificity of inhibition is a potential challenge with the development of L1 endonuclease inhibitors because this endonuclease is related to the apurinic/apyrimidinic endonuclease (human APE1), which is involved in the repair of DNA damage by the base excision repair (BER) pathway (Madhusudan et al., Nucl Acids Res, 2005, 33(15):4711-4724). As shown by FIG. 11, using a fluorescence-based in vitro cleavage assay, it was demonstrated that the present monoclonal anti-ORF2p antibody can reduce L1 endonuclease activity by about 25% without any inhibitory effect on the in vitro activity of the human APE1. These results provide evidence that the activity of L1 endonuclease can be reduced by an antibody specific to its position 205.

Overall, the data presented here demonstrate that this anti-ORF2p monoclonal antibody is useful for preventing and/or repairing genetic damage involving human L1 and for treating and/or preventing various diseases related to genetic damage in mammals.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes

The invention claimed is:

1. A binding reagent that specifically binds to human long interspersed element-1 (L1) open reading frame 2 (ORF2) protein having an endonuclease (EN) domain without an inactivating mutation at position 205, which binding reagent is selected from the group consisting of (a) an antibody having six complementarity determining regions (CDRs), which CDRs are the same as the six CDRs of monoclonal anti-L1 ORF2 protein EN antibody (hORF2 239), (b) a fragment of said antibody, said fragment having six CDRs which are the same as the six CDRs of monoclonal anti-L1 ORF2 protein EN antibody (hORF2 239) and which retains L1 ORF2 protein EN binding activity, and (c) a derivative of said antibody, said derivative having six CDRs which are the same as the six CDRs of monoclonal anti-L1 ORF2 protein EN antibody (hORF2 239), and which retains L1 ORF2 protein EN binding activity.

2. The binding reagent of claim 1, wherein said derivative of said antibody is a chimeric or a humanized antibody.

3. The binding reagent of claim 1, wherein said fragment is selected from the group consisting of a Fab, a Fab', a F(ab')$_2$, a Fv, a helix-stabilized antibody, a diabody, a single-chain Fv ("scFv"), a disulfide stabilized antibody ("dsFv"), a domain antibody ("dAb,") and a minibody.

4. The binding reagent of claim 1, wherein said antibody is monoclonal anti-L1 ORF2 protein EN antibody (hORF2 239) or a fragment of said antibody which retains L1 ORF2 protein EN binding activity.

5. The binding reagent of claim 4, wherein said antibody is monoclonal anti-L1 ORF2 protein EN antibody (hORF2 239).

6. The binding reagent of claim 4, wherein said fragment is selected from the group consisting of a Fab, a Fab', a F(ab')$_2$, a Fv; a helix-stabilized antibody, a diabody, a single-chain Fv ("scFv"), a disulfide stabilized antibody ("dsFv"), a domain antibody ("dAb,") and a minibody.

7. The binding reagent of claim 1, further wherein said binding reagent is labeled with a detectable label.

8. The binding reagent of claim 7, further wherein label is conjugated to said binding reagent.

9. The binding reagent of claim 7, further wherein label is fused to said binding reagent.

10. A hybridoma producing a monoclonal antibody which is monoclonal anti-L1 ORF2 protein EN antibody (hORF2 239).

11. The hybridoma of claim 10, which hybridoma is HORF2 hybridoma.

12. A method of detecting whether human long interspersed element-1 (L1) open reading frame 2 (ORF2) protein having an endonuclease (EN) domain without an inactivating mutation at position 205 is present in a sample, said method comprising of contacting said sample with a binding regent which specifically binds to human L1ORF2 protein with said EN domain, which binding reagent is selected from the group consisting of (a) an antibody having six complementarity determining regions (CDRs), which CDRs are the same as the six CDRs of monoclonal anti-L1 ORF2 protein EN domain antibody (hORF2 239), (b) a fragment of said antibody having six CDRs, which CDRs are the same as the six CDRs of monoclonal anti-L1 ORF2 protein EN domain antibody (hORF2 239), and which retains L1 ORF2 protein EN domain binding activity, and (c) a derivative of said antibody having six CDRs, which CDRs are the same as the six CDRs of monoclonal anti-L1 ORF2 protein EN domain antibody (hORF2 239), and which retains L1 ORF2 protein EN domain binding activity, under conditions which permit binding of the binding reagent to said protein in said sample, and detecting whether any binding reagent has bound to said protein in said sample.

13. The method of claim 12, further wherein said detection is by enzyme-linked immunosorbent assay ("ELISA").

14. The method of claim 12, further wherein said antibody is a monoclonal antibody.

15. The method of claim 14, wherein said antibody is monoclonal anti-L1 ORF2 protein EN antibody (hORF2 239) or a fragment said antibody which retains L1 ORF2 protein EN domain binding activity.

16. The method of claim 15, wherein said fragment is selected from the group consisting of a Fab, a Fab', a F(ab')$_2$, a Fv; a helix-stabilized antibody, a diabody, a single-chain Fv ("scFv"), a disulfide stabilized antibody ("dsFv"), a domain antibody ("dAb,") and a minibody.

17. The method of claim 12, further wherein said binding reagent is labeled with a detectable label.

18. The method of claim 12, further wherein label is conjugated to said binding reagent.

* * * * *